(12) United States Patent
Ellins

(10) Patent No.: US 12,228,511 B1
(45) Date of Patent: Feb. 18, 2025

(54) ORGANIC PLANT MATERIAL MICROBIAL TEST KIT DEVICES AND PROCESSING METHOD

(71) Applicant: Craig Ellins, Las Vegas, NV (US)

(72) Inventor: Craig Ellins, Las Vegas, NV (US)

( * ) Notice: Subject to any disclaimer, the term of this patent is extended or adjusted under 35 U.S.C. 154(b) by 0 days.

(21) Appl. No.: 18/372,669

(22) Filed: Sep. 25, 2023

(51) Int. Cl.
*G01N 21/64* (2006.01)
*G01N 21/33* (2006.01)

(52) U.S. Cl.
CPC ............. *G01N 21/64* (2013.01); *G01N 21/33* (2013.01); *G01N 2201/12* (2013.01)

(58) Field of Classification Search
CPC ................................ G01N 21/64; G01N 21/33
USPC ............................................... 422/82; 702/19
See application file for complete search history.

(56) References Cited

U.S. PATENT DOCUMENTS

| | | | | | |
|---|---|---|---|---|---|
| 2,771,398 | A | * | 11/1956 | Snyder ................... | C12M 41/36 435/805 |
| 3,676,321 | A | * | 7/1972 | Cummings ........ | G01N 33/1806 205/780 |
| 3,929,583 | A | * | 12/1975 | Sharpe ................... | C12M 47/04 435/297.5 |
| 3,968,010 | A | * | 7/1976 | Young ................... | C12Q 1/045 435/287.7 |
| 4,732,680 | A | * | 3/1988 | Weaver ................. | C02F 3/1231 210/908 |
| 5,403,722 | A | * | 4/1995 | Floeder ................. | G06M 11/00 435/39 |
| 5,462,860 | A | * | 10/1995 | Mach ..................... | C12M 25/06 435/243 |
| 5,510,246 | A | * | 4/1996 | Morgan ................. | C12M 41/36 435/808 |
| 5,573,950 | A | * | 11/1996 | Graessle ................ | C12M 23/04 422/561 |
| 5,601,998 | A | * | 2/1997 | Mach ...................... | C12N 1/20 435/34 |
| 5,627,045 | A | * | 5/1997 | Bochner ................. | C12Q 1/04 435/822 |
| 5,882,882 | A | * | 3/1999 | Bochner ................. | C12Q 1/04 435/7.31 |

(Continued)

FOREIGN PATENT DOCUMENTS

WO  WO-2008063192 A1 * 5/2008 ......... G01N 15/1463

*Primary Examiner* — Arlen Soderquist
(74) *Attorney, Agent, or Firm* — Edmond DeFrank

(57) ABSTRACT

The embodiments disclose a portable microbial test kit including a plurality of organic materials configured to be processed for preservation and prevention of mold, bacteria infestations, rot, and decay and reduce and prevent any degradation, a storage facility, a plurality of hardware, and a plurality of equipment configured for storage and monitoring of the plurality of organic materials, wherein the hardware and the equipment are configured to monitor the condition of the organic materials during storage, a plurality of components coupled to the hardware and the equipment configured to electronically monitor the condition of the organic materials during storage, at least one electronic device coupled to the plurality of hardware and the plurality of equipment configured to report electronically the condition of the organic materials to the facility and customer, and a system coupled to the at least one electronic device configured for customers to automatically reorder hardware and equipment.

20 Claims, 33 Drawing Sheets

(56) References Cited

U.S. PATENT DOCUMENTS

| | | | | |
|---|---|---|---|---|
| 5,989,853 A * | 11/1999 | Bochner | C12Q 1/04 | 435/32 |
| 6,107,054 A * | 8/2000 | Gibbs | C12Q 1/04 | 422/50 |
| 6,271,022 B1 * | 8/2001 | Bochner | G01N 35/028 | 422/65 |
| 10,255,670 B1 * | 4/2019 | Wu | H04N 7/183 | |
| 2001/0024805 A1 * | 9/2001 | Williams | B01L 3/5085 | 435/305.1 |
| 2002/0110906 A1 * | 8/2002 | Bedingham | C12M 23/04 | 435/39 |
| 2002/0132021 A1 * | 9/2002 | Raskin | A01H 3/00 | 424/773 |
| 2003/0186350 A1 * | 10/2003 | Newell | C12M 41/46 | 435/283.1 |
| 2004/0092001 A1 * | 5/2004 | Bedingham | C12M 25/02 | 435/286.2 |
| 2004/0101189 A1 * | 5/2004 | Green | G06V 20/69 | 382/133 |
| 2004/0102903 A1 * | 5/2004 | Graessle | G01N 15/1433 | 702/19 |
| 2004/0126365 A1 * | 7/2004 | Villamar | G16H 50/80 | 702/19 |
| 2004/0177011 A1 * | 9/2004 | Ramsay | G06Q 10/06 | 705/28 |
| 2005/0053265 A1 * | 3/2005 | Graessle | C12M 41/36 | 382/128 |
| 2005/0053266 A1 * | 3/2005 | Plumb | G06V 20/69 | 382/128 |
| 2005/0216291 A1 * | 9/2005 | Shaheen | H01G 4/228 | 705/1.1 |
| 2006/0172370 A1 * | 8/2006 | Hirleman | G01N 21/4788 | 359/368 |
| 2007/0281288 A1 * | 12/2007 | Belkin | G01N 21/6452 | 435/287.1 |
| 2008/0102487 A1 * | 5/2008 | Yao | G01N 21/31 | 506/4 |
| 2008/0144697 A1 * | 6/2008 | Stewart | G01K 1/024 | 374/E1.004 |
| 2008/0199904 A1 * | 8/2008 | Suslick | C12M 37/04 | 435/288.7 |
| 2009/0181449 A1 * | 7/2009 | Markin | C12M 23/42 | 703/11 |
| 2010/0159504 A1 * | 6/2010 | Babico | G01N 15/1459 | 435/288.7 |
| 2011/0033847 A1 * | 2/2011 | Walsh | C12Q 1/04 | 435/6.16 |
| 2011/0143334 A1 * | 6/2011 | Roscoe | C12M 25/06 | 435/5 |
| 2011/0150314 A1 * | 6/2011 | Bolea | C12M 41/48 | 382/133 |
| 2011/0151501 A1 * | 6/2011 | Bolea | C12M 23/44 | 435/287.1 |
| 2011/0153220 A1 * | 6/2011 | Bolea | G01N 35/00732 | 702/19 |
| 2011/0158499 A1 * | 6/2011 | Bolea | C12Q 1/045 | 382/133 |
| 2011/0171683 A1 * | 7/2011 | Mach | C12Q 1/04 | 435/39 |
| 2011/0244511 A1 * | 10/2011 | Mach | C12Q 1/04 | 435/39 |
| 2011/0256531 A1 * | 10/2011 | Rajagopal | C12Q 1/04 | 435/7.1 |
| 2012/0028297 A1 * | 2/2012 | Zook | C12Q 1/24 | 435/287.7 |
| 2012/0094327 A1 * | 4/2012 | Young | C12M 23/20 | 435/39 |
| 2012/0114218 A1 * | 5/2012 | Atkin | C12M 41/36 | 382/133 |
| 2012/0273569 A1 * | 11/2012 | Dlott | G06Q 10/063 | 235/375 |
| 2012/0301911 A1 * | 11/2012 | Roscoe | C12Q 1/54 | 435/28 |
| 2012/0308988 A1 * | 12/2012 | Discenzo | G05B 13/04 | 435/286.1 |
| 2013/0109051 A1 * | 5/2013 | Li | G06T 7/0012 | 435/288.7 |
| 2013/0316393 A1 * | 11/2013 | Swanson | C12Q 1/04 | 210/236 |
| 2013/0344202 A1 * | 12/2013 | Addison | A23L 33/105 | 426/649 |
| 2014/0219538 A1 * | 8/2014 | Guthrie | G06V 20/69 | 382/133 |
| 2014/0220610 A1 * | 8/2014 | Chandrapati | C12Q 1/04 | 435/19 |
| 2015/0064703 A1 * | 3/2015 | Super | G01N 33/56938 | 435/6.12 |
| 2015/0086982 A1 * | 3/2015 | Becker | C12Q 1/6895 | 435/6.11 |
| 2015/0196002 A1 * | 7/2015 | Friesth | A01G 7/045 | 315/297 |
| 2015/0237807 A1 * | 8/2015 | Valiquette | A01G 27/02 | 47/66.7 |
| 2015/0283276 A1 * | 10/2015 | Janisiewicz | A01N 63/32 | 424/93.51 |
| 2015/0339513 A1 * | 11/2015 | Bolea | G06V 20/698 | 382/133 |
| 2015/0373923 A1 * | 12/2015 | Ferrell | A01G 7/06 | 800/313 |
| 2016/0034745 A1 * | 2/2016 | Couture | G01N 15/1433 | 382/133 |
| 2016/0075988 A1 * | 3/2016 | Halverson | C12M 23/24 | 435/39 |
| 2016/0083773 A1 * | 3/2016 | Triva | C12M 41/36 | 435/309.1 |
| 2016/0139027 A1 * | 5/2016 | Teramura | C12Q 1/02 | 382/133 |
| 2016/0194597 A1 * | 7/2016 | Miyajima | G06T 7/0012 | 382/133 |
| 2017/0073629 A1 * | 3/2017 | Chandrapati | C12Q 1/04 | |
| 2017/0094920 A1 * | 4/2017 | Ellins | A01H 4/001 | |
| 2017/0219485 A1 * | 8/2017 | Bae | G01N 21/47 | |
| 2017/0240949 A1 * | 8/2017 | Brutinel | C12M 37/04 | |
| 2017/0355943 A1 * | 12/2017 | Brutinel | C12Q 1/04 | |
| 2018/0146618 A1 * | 5/2018 | Elazary | A01D 46/30 | |
| 2018/0349671 A1 * | 12/2018 | Bouthillon | C12Q 1/06 | |
| 2018/0369437 A1 * | 12/2018 | Grossman | A61L 2/24 | |
| 2019/0011882 A1 * | 1/2019 | Gusyatin | G01N 15/1433 | |
| 2019/0050948 A1 * | 2/2019 | Perry | G06F 30/27 | |
| 2019/0120836 A1 * | 4/2019 | Di Domenico | G01N 35/0098 | |
| 2019/0212269 A1 * | 7/2019 | Liebsch | C09K 11/06 | |
| 2020/0048679 A1 * | 2/2020 | Chandrapati | C12Q 1/10 | |
| 2020/0051015 A1 * | 2/2020 | Davis | G06K 19/0723 | |
| 2020/0056136 A1 * | 2/2020 | Brutinel | C12M 1/16 | |
| 2020/0056219 A1 * | 2/2020 | Young | C12Q 1/04 | |
| 2020/0057288 A1 * | 2/2020 | Schulze | G06T 5/80 | |
| 2020/0078433 A1 * | 3/2020 | Wilkie | A61K 8/97 | |
| 2020/0109431 A1 * | 4/2020 | Chandrapati | C12M 41/36 | |
| 2020/0111342 A1 * | 4/2020 | Hummer | H04M 1/72412 | |
| 2020/0184153 A1 * | 6/2020 | Bongartz | A01G 9/249 | |
| 2020/0193140 A1 * | 6/2020 | Papermaster | G06V 20/693 | |
| 2020/0279374 A1 * | 9/2020 | King | G06V 10/50 | |
| 2020/0302338 A1 * | 9/2020 | Carroll | A01G 27/00 | |
| 2020/0354667 A1 * | 11/2020 | Papermaster | G16B 50/00 | |
| 2021/0302402 A1 * | 9/2021 | DeSanto | G05D 1/0094 | |
| 2021/0339295 A1 * | 11/2021 | Louis DeSanto | H02J 50/30 | |
| 2021/0375390 A1 * | 12/2021 | Fuxman | G06Q 10/04 | |
| 2021/0382026 A1 * | 12/2021 | Narula | G01N 21/03 | |
| 2021/0389243 A1 * | 12/2021 | Sela | C12Q 1/04 | |
| 2022/0132748 A1 * | 5/2022 | Vild | G16B 40/30 | 47/1.7 |
| 2022/0139527 A1 * | 5/2022 | Eineren | G16H 30/20 | 705/2 |
| 2022/0153416 A1 * | 5/2022 | Nicodemos | G05D 1/0016 | |
| 2022/0178793 A1 * | 6/2022 | Re | H04N 23/61 | |
| 2022/0213421 A1 * | 7/2022 | Young | C12M 23/20 | |
| 2022/0309595 A1 * | 9/2022 | England | G06Q 10/06315 | |

(56) References Cited

U.S. PATENT DOCUMENTS

| | | | |
|---|---|---|---|
| 2023/0026679 A1* | 1/2023 | Matarazzo | B64C 39/024 |
| 2023/0039403 A1* | 2/2023 | De Santo | B64D 1/18 |
| 2023/0401449 A1* | 12/2023 | Özel Duygan | G06F 18/24137 |

* cited by examiner

INVENTORY SYSTEM

PO Created Customer

- The Growbial System** (HARDWARE) Pelican Case, Incubator, Grinder, Beakers, Permanent Bar Codes, QR Scanner, Photo Up-Loader, Tablet, Utility Belt or apron, Isopropyl spray bottle, Mortar and Pestle, Nitrogen Spray, forceps, K82 (TSB), USP, 10 ML 16X125 MM glass tube, and K109 Butterfields phosphate Buffer 9ml fill 16x125 mm tube
- EXPENDABLES: Petri Dish (Dish A, Mold & Yeast), Petri Dish (Dish B, Bacteria), Petri Dish (Dish C, Water), Petri Dish (D, Flower Test), Compact Dry Dish (Dish E Flower Test), Gloves
- Hazard Bags or Tape for box, Polyester Tip Swabs, Pipettes for Water Collecting, Sterile Blended Bags, Instructional Manual, Compartment Custom Cardboard Package (Bio-Insert), Shipping Box, Soy Liquid
- Items incl 100 dishes - Must refrigerate
- Every month, after customer receives first shipment, customer gets 100 additional tests automatically for The Air & Surface Test, and 20 for The Flower Test - (Or more if they order more ala cart, 10 at a time, or rounded to the next highest 10). They can order from their own customer portal that connects to the shopping cart. Menu to be created for shopping cart based on _item spreadsheet._
- All other expendables will be ala cart that can ordered by a permanent bar code on the KIT

→

- FOR EXAMPLE: Customer needs more gloves. They take their QR code reader and swipe the GLOVES QR CODE on the kit box and it automatically opens the shopping cart and places the order. The scan order will go to their own customer portal that also connects to the shopping cart.

→

- Same for all expendables*** EXCEPT PETRI DISHES - 100 will be sent every month based on their sign-up date. We should ship EVERY Tuesday.

FIG. 3

INVENTORY SYSTEM (Part 2) 400

PO Created Vendor
No hardware will be kept on site - Kits will be made to order. When the customer places an order, the system can make a Purchase Order (PO) for each vendor when a kit is ordered.

*For example: Incubator from XYZ, QR code Scanner from ABC, etc.*

- The system generates the PO for each separate vendor and sends to the Manager to send to the vendor.
- The manager will follow through with the vendor to make sure the item is ordered.
- The manager will know when the parts arrive, when it is put inside a kit, and when it is shipped by us and received by customer.
- Once all other expendable inventory reaches a 30% volume we re-order from our vendors. Notification to manager should occur.
- If customer wants more hardware (i.e., incubator, scanner gun, etc) they should be able to order from their customer portal ala cart shopping cart, as part of the menu of things to order.
- As customer scans dish at their facility, they get notification in their back office and we get notification in real time as they are used - then our admin portal.
- Our admin portal will have a summary page of all customer inventory in real time to maintain and monitor. link to the customers personal page

FIG. 4

CUSTOMER PORTAL

*500*

When customer logs in:

1. Create username and password
2. Confirm customer info
3. Name each permanent location QR code placement disc in their account.
4. Review SOPs
5. Review Instructional Videos
6. Review Shopping cart (menu of all expendables and hardware)
7. Display Purchase history
8. Access to Tracking of each dish with date and time of movement, (placement, pickup, incubator photo, disposal [Same info we receive but specific to each customer])
9. Personal Inventory of expendables (customer's previous orders and autoshipments)
10. Final Reports - We provide a template for data to be filled in for each test with track and trace date and time, CFU and identification data to come from AI.
11. Allow customer to document cleaning or remediation actions taken after the report is given (ie., clean affected area, ozoned dry room, etc.)
12. Access to Remediation techniques
13. Summary page of all tests

FIG. 5

MANUFACTURING, PACKAGING, SHIPPING

Manufacturing
- Real Time Inventory. When something leaves or arrives, it is checked in and out and listed on an current inventory sheet of raw materials, hardware and expendables
- Raw Materials must be included
- Cost of Goods included with cost of items
- Quality Assurance (QA) Checklist for Manager to ensure all dishes are made properly and some kind of sign off
- QR code Generator for dishes – with printing

Packing
- Inventory of all Packing Materials (boxes, plastic sealer, filler, tape, labels, postage, etc.)
- Shipping Label generator
- Label generator for logos

Shipping
- Notification when something goes out and when something comes in and will be checked in and out by manager
- Notification of when customer receives all shipped items.

FIG. 6

CUSTOMER TRACK AND TRACE

- Customer receives package - (notification as previously stated)
- Triggers email to customer alerting package has been delivered with 'Welcome Packet' and quick start guide attachment
- Ability to generate template based emails, as well as new custom emails to go to customers as needed
- Schedule Live Zoom Demo, or in person demonstration
- Watch Video of items received, tutorial videos and other educational videos
- QR scanner activation - linking scanner to customer and portal - has a simple sample to insure connectivity
- System asks for QR code permanent placement information - Cannot move forward without this activity being completed
- QR reader is used to track placement, pickup, incubator, photo, disposal tracking time, date and location [Same info we receive during activity but specific to each customer in their personal customer portal account]
- After incubation, a, picture is taken
- System analyzes image and QR code in picture
- Picture check to ensure quality of image (blurry, out of frame, etc.)
- Picture sent to AI
- AI reads dish, sends results (mold ID and CFU count back to reporting system for display in customer's back office with auto fill on template with printing and PDF capabilities)
- AI Assigns GREEN - YELLOW - RED designation based on CFU numbers
- System places picture on the report, including location of sample, and results

FIG. 7

COA REPORT — 800

To Include: See next figure.

1. AI reads dish, sends results back to 24 hours after incubation period (mold ID and CFU count back to reporting system for display in customer's back office with auto fill on template with printing and PDF capabilities) and assigns GREEN - YELLOW - RED designation based on CFU numbers
2. Customer name and number, QR code of each dish and permanent placement name, for example: VEG 1 Tray 2 L
3. Date of Report
4. Picture of dish with QR code
5. Permanent placement information
6. Date and time of placement, incubation time in and out, photo
7. Mold identification
8. CFU Count - Green Yellow Red
9. Suggested Remediation
10. Document any notes before final print
11. Allow customer to add additional email address to receive reports (i.e., Director of Cultivation)

FIG. 8

COA REPORT

EZ MICRO LABS

CO: Example Labs
BIO-INSERT: YMR (Mold and Yeast)
PERMANENT MARKER: 28 - mother room
DESCRIPTION: nutrient tank, on your right

TIMES AND DATES:
Placement: Day 00/00/0000 | 00:00 AM
Pickup: Day 00/00/0000 | 00:00 AM
Placed in Incubator: Day 00/00/0000 | 00:00 AM
Photographed: Day 00/00/0000 | 00:00 AM

EZMICROLABS.COM

QR CODE — 920

ABcdefGHiJ0KI2M34Nop
Z5AbcdEfGHIJk678lmnopQ9
AB1Cde1FGhijKlmNOPqRsT

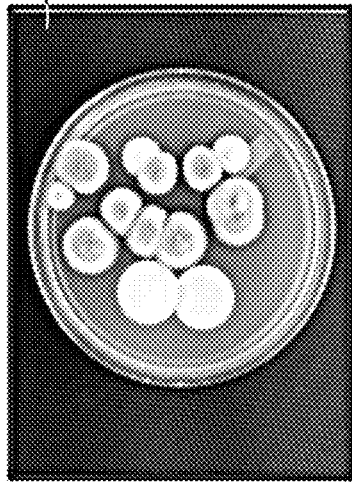
910

DISH TYPE: Mold & Yeast
Mold ID: YMR   CFU COUNT: 000 - STATUS
Next Steps:
_____
_____

CFU Scale

FIG. 9

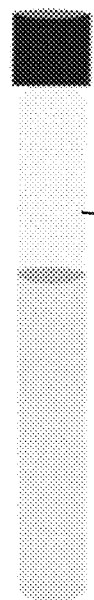
2700
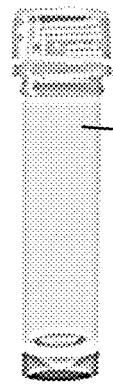
2710
FIG. 27A   FIG. 27B
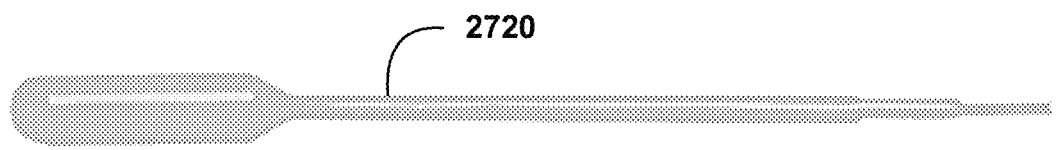
2720
FIG. 27C
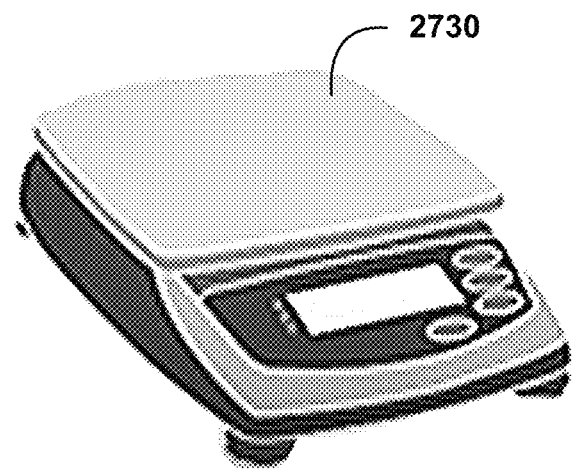
2730
FIG. 27D ive purposes only an example
ORGANIC PLANT MATERIAL MICROBIAL TEST KIT DEVICES AND PROCESSING METHOD

BACKGROUND

Processing of organic materials for preservation until use is plagued with problems of degradation of the organic materials. Mold, bacteria infestations, rot, and decay can change the quality and valuable characteristics of organic materials. The degradation can cause a complete loss of the crop and at least a decline in the commercial value of the organic materials crop marketability and market value. Critical processing steps and planning can reduce and even prevent any degradation from taking place.

BRIEF DESCRIPTION OF THE DRAWINGS

FIG. 3 shows a block diagram of an overview of Part 1 showing a block diagram of a PO-created customer of one embodiment.

FIG. 4 shows a block diagram of an overview of Part 2 showing a block diagram of an overview of a PO-created vendor of one embodiment.

FIG. 5 shows a block diagram of an overview of a customer portal of one embodiment.

FIG. 6 shows a block diagram of an overview of the manufacturing, packaging, and shipping of one embodiment.

FIG. 7 shows a block diagram of an overview of customer trace and track of one embodiment.

FIG. 8 shows a block diagram of an overview of information in a report of one embodiment.

FIG. 9 shows a block diagram of an overview of an example of a report of one embodiment.

FIG. 27A shows for illustrative purposes only an example of a YMR Activating Solution of one embodiment.

FIG. 27B shows for illustrative purposes only an example of a Buffer B Solution of one embodiment.

FIG. 27C shows for illustrative purposes only an example of a Pipette of one embodiment.

FIG. 27D shows for illustrative purposes only an example of a flower and plant material measuring scale of one embodiment.

DETAILED DESCRIPTION OF THE INVENTION

In the following description, reference is made to the accompanying drawings, which form a part hereof, and which are shown by way of illustration a specific example in which the invention may be practiced. It is to be understood that other embodiments may be utilized and structural changes may be made without departing from the scope of the present invention.

General Overview:

It should be noted that the descriptions that follow, for example, in terms of an organic material processing method and devices are described for illustrative purposes and the underlying system can apply to any number and multiple types of organic materials. In one embodiment of the present invention, the organic material processing method and devices can be configured using multiple styles of organic materials storage devices. The organic material processing method and devices can be configured to include petri dish culturing and can be configured to include mitigation of infected organic materials using the present invention.

Figure 1:
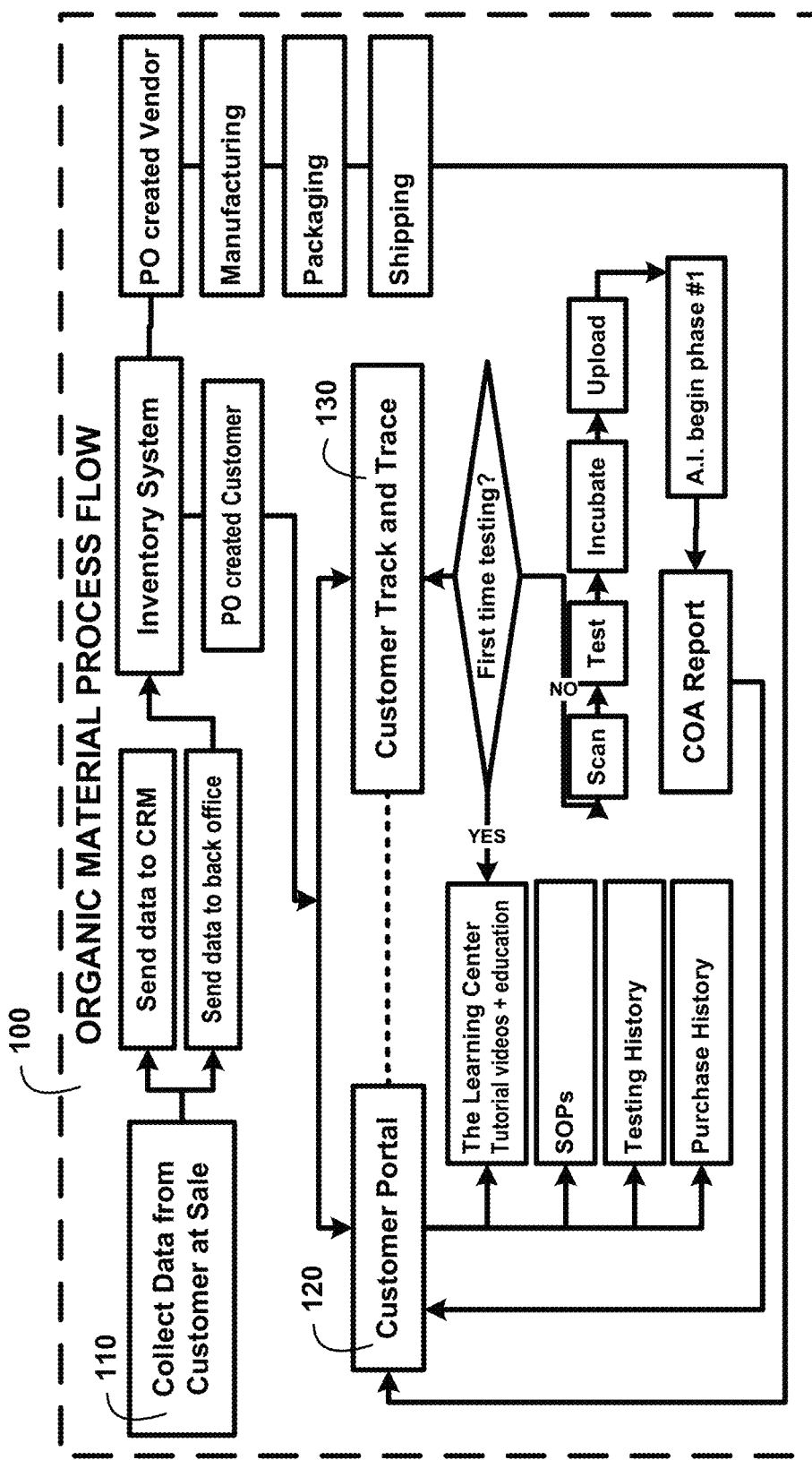
FIG. 1 shows for illustrative purposes only an example of an overview of an organic materials process flow of one embodiment.

FIG. 1 shows for illustrative purposes only an example of an overview of an organic materials process flow of one embodiment. FIG. 1 shows an organic materials process flow 100 for processing organic materials for preservation and prevention of mold, bacteria infestations, rot, and decay and to reduce and prevent any degradation. The organic materials process flow 100 includes a process to collect data from a customer at sale 110. The customer data is processed to send data to CRM, a customer relationship management system.

The customer data is also processed to send data to the back office. The organic materials process flow 100 includes a customer portal 120 allowing a customer to order from the customer portal. A Customer Track and Trace 130 system in the process flow generates test results reports for the customer that include colony forming units (CFU) and other testing data.

A process includes providing a storage facility, hardware, and equipment for storage and monitoring of the organic materials, storing organic materials in hardware and equipment configured for monitoring the condition of the organic materials during storage and gathering the condition of the organic materials during storage electronically using components of the hardware and equipment. Processing includes reporting electronically the condition of the organic materials to the facility and customer.

The method includes providing a system for customers to reorder hardware and equipment automatically of one embodiment. The process allows the owner to pack and store their organic materials.

DETAILED DESCRIPTION

The process allows an organic materials owner to measure the organic contents for mold, bacteria, rot, and decay for the owner packing and storing their organic materials. While being stored, the organic materials are monitored periodically to detect and mitigate any mold, bacteria, rot, and decay infestations. The owner of the organic materials may not have been aware of the mold and bacteria present in their organic materials. Periodic monitoring and testing provide early detection, providing the owner with a chance to mitigate the infestation and preserve at least a portion of the organic materials of one embodiment.

Figure 2:
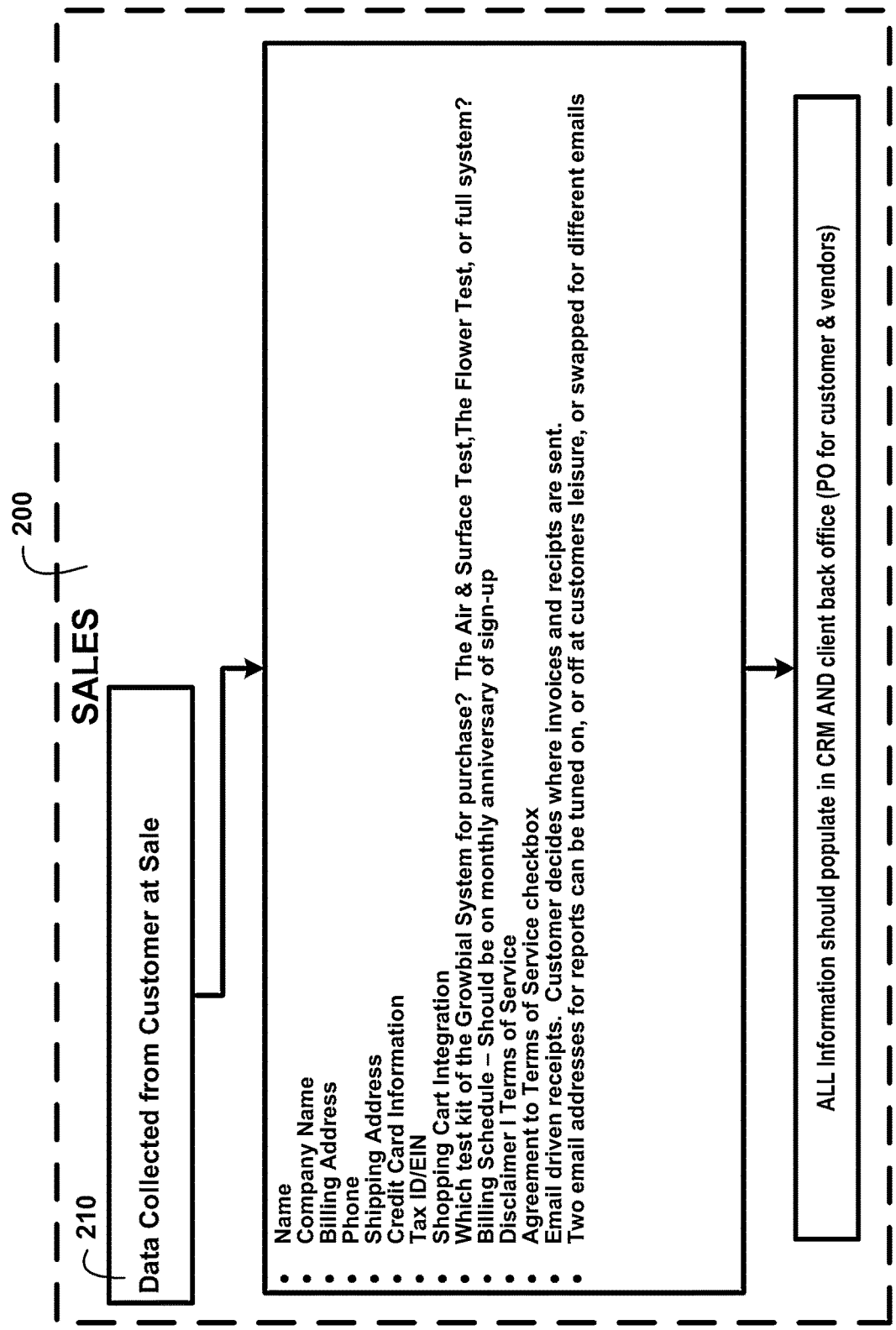
FIG. 2 shows a block diagram of an overview of data collected from the customer at the sale of one embodiment.

FIG. 2 shows a block diagram of an overview of data collected from a customer of one embodiment. FIG. 2 shows sales 200 data collected from a customer at sale 210. An owner packing and storing their organic materials is a normal operation. The owner of the organic materials may not be aware of mold and bacteria that are present in their organic materials. Periodic monitoring and testing provide early detection 220. The testing includes multiple testing processes including The Air & Surface Test and The Flower Test. In this process, the stored organic materials are monitored periodically to detect and mitigate any mold, and bacteria infestations 230. The process includes systems and treatments to eradicate the mold and bacteria 240. The treatments mitigate the infestation and preserve at least a portion of the organic materials 250. Processing organic materials for preservation and prevention of mold, bacteria infestations, rot, and decay and to reduce and prevent any degradation 260 of one embodiment.

The sales data includes Customer Name, Company Name, Billing Address, Phone, and Shipping Address. Additionally, the data will include the customer's credit card (CC) information and their signature, and to agree to be charged every month, the customer verifies via agreement to Terms & Services at check out. The customer decides which Test Kit they would like to purchase; The Air & Surface Test, The Flower Test, or ala cart, depending on what they wish to order.

The data displays a Disclaimer and Terms of Service Agreement. A billing schedule is then set up by the anniversary of sign-up. The customer provides an email address for email-driven receipts, and the customer decides where invoices and receipts go. ALL information populates in a CRM, as well as the customer and client back office of one embodiment.

A PO Created Customer:

FIG. 3 shows a block diagram of an overview of Part 1 showing a block diagram of a PO-created customer of one embodiment. FIG. 3 shows part 1 of an inventory system 300 for a purchase order (PO) created by a customer. The PO created by customer 310 orders a full Test Kit or orders supplies and tools ala cart as needed by the customer.

The Test Kit includes at least an apron 1800, YMR bio-insert rack-open 1900, the air & surface test 2000, mobile tool station 2300, incubator front view 2400, EZ photo stand 2500, spray bottle 2510, sterile blended bag 2600, YMR activating solution 2610, buffer solution(s) 2700, buffer b 2710, pipette 2720, sterile swab 2800, forceps 2810, hazard stickers 2820, permanent incubator sticker 2900, permanent locator sticker 2920, instructional manual, compartment custom cardboard package (Bio Inserts, FIGS. 19-23), shipping box, and soy liquid. Items include 100 dishes that hold organic materials cultures that the customer must refrigerate for one embodiment.

Every month based on the sign-up date, the customer receives the first shipment, and depending on which system and test they bought, the customer receives 100 tests of The Air & Surface Test, and 20 tests of The Flower Test automatically. Additional items can be purchased through the customer portal, ala cart, which also connects to a shopping cart. Menu to be created for shopping cart based on item spreadsheet. All other expendables will be in Ala Cart that customers can order by a permanent QR code on the kit or through the customer portal.

For example: if the customer needs more gloves; they take their QR code reader and swipe the gloves' QR code on the kit box and it automatically opens the shopping cart and places the order. The scanned order will go to the customer portal that connects to the shopping cart. Same for all expendables except petri dishes—100 will be sent every month based on their sign-up date of one embodiment.

Part 2 a PO created vendor:

FIG. 4 shows a block diagram of an overview of Part 2 showing a block diagram of an overview of a PO-created vendor of one embodiment. FIG. 4 shows a PO-created vendor 410. Part 2 of an inventory system 400 is for a purchase order (PO) created vendor. In the case of a PO Created Vendor, no hardware will be kept on-site-Kits will be made to order. When the customer places an order, the software system will make a PO for each vendor when a kit is ordered. For example: Incubator from XYZ, QR code Scanner from ABC, etc.

The system can generate the PO for each separate vendor and send it to the manager to send to the vendor. The manager will follow through with the vendor to make sure the item is ordered. Then the manager will know when the parts arrive, when they are put inside a kit, and when it is shipped by us and received by the customer. Once all other expendable inventory reaches a 30% volume, we re-order from our vendors. A notification to the manager occurs.

If a customer wants more hardware (i.e., incubator, QR scanner, etc.) they should be able to order from their customer portal, ala cart shopping cart, part of the menu of things to order. As the customer scans a dish at their facility, they get a notification in their back office, and we get a notification in our admin portal. Our admin Portal will have a summary page of all customer inventories in real-time as they are used-then link to the customer's personal page to maintain and monitor of one embodiment.

A Customer Portal:

FIG. 5 shows for illustrative purposes only an example of a customer portal of one embodiment. FIG. 5 shows a customer portal 500 available to the customer for making orders and receiving reports and other communications. When a customer logs in, they can create a username and password, and confirm their customer information. The customer is queried to name each permanent location QR code placement sticker (part of the test) in their account. On the customer portal 500 a customer can review SOPs and Instructional Videos on how to operate the equipment and prepare organic materials cultures.

The customer portal 500 also provides the customer with a review of their shopping cart with a menu of all expendables and hardware they may need to order. A Display Purchase history will inform the customer of their last orders. The customer portal 500 also provides access to tracking each dish (test) with date and time of movement, placement, pickup, incubator, photo, and disposal. This is the same information we receive, but specific to each customer.

A personal inventory of expendables provides what the customer has used and what they need, as well as what their auto-ship arrangements are. The customer may also access the Final Reports-we provide a template for data to be filled in for each test with track and trace date, time, CFU, and identification data to come from our artificial intelligence (AI) system and devices. The customer portal allows the customer to document cleaning or remediation actions taken after the report is given, i.e., clean affected areas, ozone dry room, etc. Access to remediation techniques they should use, and a summary page of all tests for their organic materials of one embodiment.

Manufacturing, Packaging, and Shipping:

FIG. 6 shows for illustrative purposes only, an example of manufacturing, packaging, and shipping of one embodiment. FIG. 6 shows the manufacturing, packaging, and shipping 600 processes including for manufacturing Real Time Inventory. Also, for manufacturing 610, when something leaves or arrives, it is checked in and out and listed on a current inventory sheet of raw materials, hardware, and expendables, and raw materials must be included.

A Cost of Goods (COG) is included with the cost of items for the customer, including shipping costs if applicable. A quality assurance (QA) checklist for managers to ensure all dishes are made properly and with a sign-off by the party preparing the dish. A QR code generator for dishes with printing is used to identify correctly the dish, source, date, and other information to track the dish culture.

Packaging 620 processes include an Inventory of all Packing Materials (boxes, plastic sealer, filler, tape, labels, postage, etc.). A shipping label generator and label generator for logos are used to confirm the shipping location as provided by the customer and any company logos. Shipping 630 processes include notification when something goes out and when something comes in and will be checked in and out by the manager. The Manager will also receive a notification of when the customer receives all shipped items of one embodiment.

Customer Trace and Track:

FIG. 7 shows for illustrative purposes only an example of a customer trace and track of one embodiment. FIG. 7 shows a customer trace and track 700 processes and systems. A Customer receives the package and a notification as previously stated, is received. The notification triggers an email to the customer alerting that the package has been delivered with the Welcome Packet and Quick Start Guide attachment. The customer track and trace 700 processes and systems can generate template-based emails, as well as new custom emails to go to customers as needed. Customers can schedule a live Zoom demo of the products and procedures or an in-person demo. Customers can watch videos of items received, tutorial videos, and other educational videos. QR code scanner activation—linking scanner to customer and portal—has a simple sample to ensure connectivity.

The System asks for a QR code permanent placement information—cannot move forward without this activity being completed. A QR code reader is used to track placement, pickup, incubator, photo, disposal tracking time, date, and location, this is the same information we receive during activity, but specific to each customer in their customer portal account. After incubation, a picture is taken. The system analyzes the image and QR code in the picture. A Picture check is performed to ensure the quality of the image (blurry, out of frame, etc.).

The picture is then sent to AI. AI reads the dish and sends the results (mold ID and CFU count back to a reporting system for display in the customer's back office with auto-fill on template with printing and PDF capabilities). The AI Assigns GREEN-YELLOW-RED designation based on CFU numbers (FIG. 10) and provides those CFU numbers of one embodiment. The System places the picture on the report including the location of the sample and results.

A COA Report:

FIG. 8 shows a block diagram of an overview of information in a COA report of one embodiment. FIG. 8 shows a COA report 800 generated by the AI system and devices.

The COA report provides the mold ID and CFU count of the tested plant materials. The AI reads the dish, sends results back after the incubation period (mold ID and CFU count back to reporting system for display in customer's back office with auto fill on the template with printing and PDF capabilities), and assigns GREEN-YELLOW-RED designation based on CFU numbers. The customer's name, number, and QR code of each dish and permanent placement name: for example, VEG 1, Tray 2L. The AI report format includes the information described in FIG. 9 and shows the photo of the dish culture with any, if present, infestation of one embodiment.

A Certified Report:

FIG. 9 shows a block diagram of an overview of an example of a certified report of one embodiment. FIG. 9 shows a certified report 900. The certified report 900 also includes a date of report, a picture of dish 910 with QR code number 920, permanent placement information, date and time of placement, incubation in and out time, photo, mold identification, and CFU count numbers-GREEN, YELLOW, RED. Suggested remediation accompanies the report. The report includes any additions to the document, as well as any notes before final printing. The AI system and devices allow the customer to add additional email addresses to receive reports (i.e., Director of Cultivation) of one embodiment.

Figure 10:
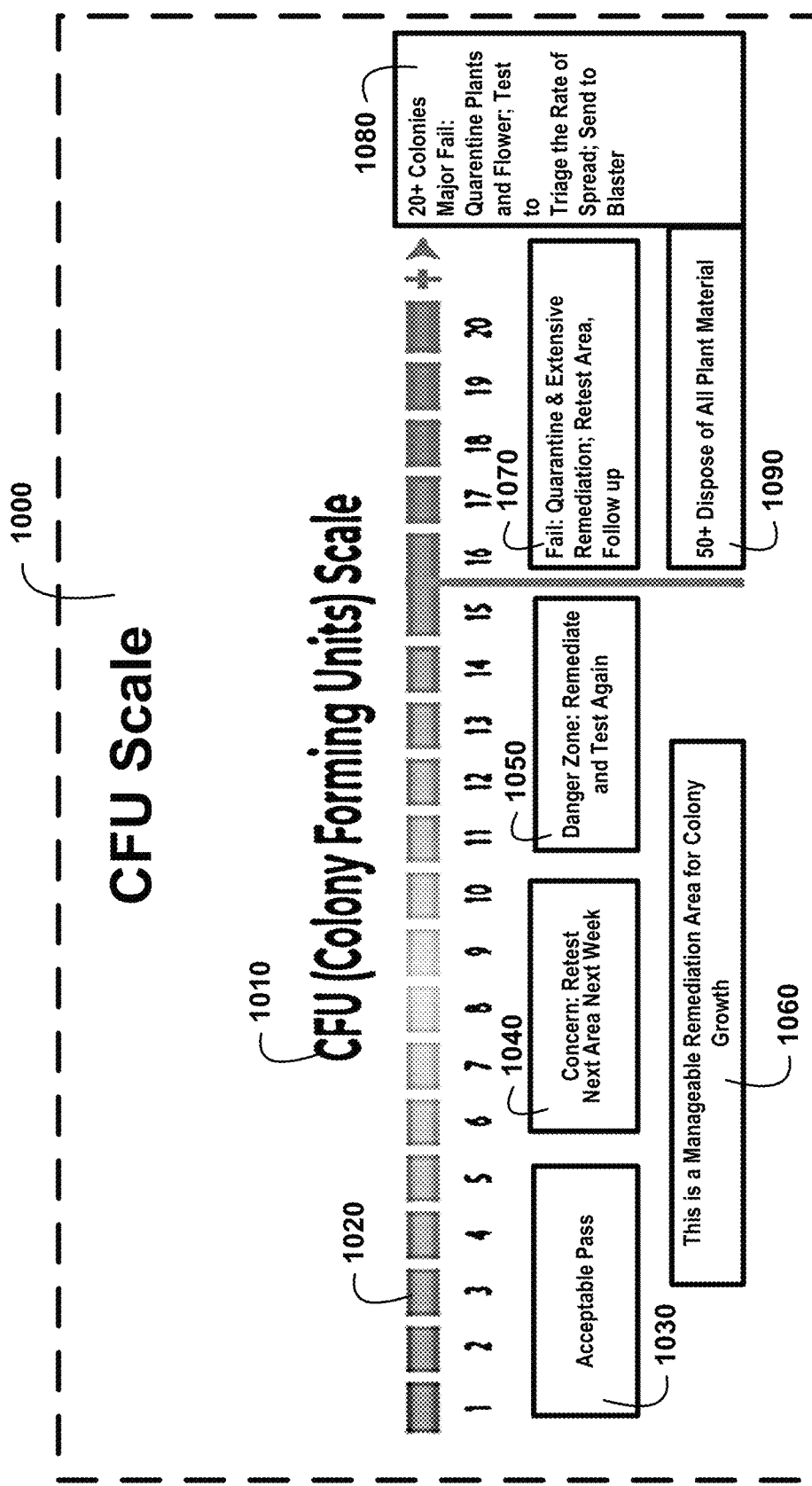
FIG. 10 shows for illustrative purposes only an example of a report of the CFU Scale of one embodiment.

A Report on the CFU Scale:

FIG. 10 shows for illustrative purposes only an example of a report of the CFU Scale of one embodiment. FIG. 10 shows an AI report format of a CFU Scale 1000. The report includes a CFU (Colony Forming Units) Scale 1010. The CFU Scale shows unit counts from 1 to 20+ 1020. Acceptable unit counts receive an acceptable pass 1030. Unacceptable unit counts receive various levels of action related to the plant materials. For example, Concern: Retest next area next week 1040, Danger zone: remediate and test again 1050 This is a manageable remediation area for colony growth 1060, Fail: quarantine & extensive remediation; retest area, follow-up 1070, 20+ colonies major fail: quarantine plants and flower; test to triage the rate of spread; send to blaster 1080, and 50+ dispose of all plant material 1090.

Figure 11:
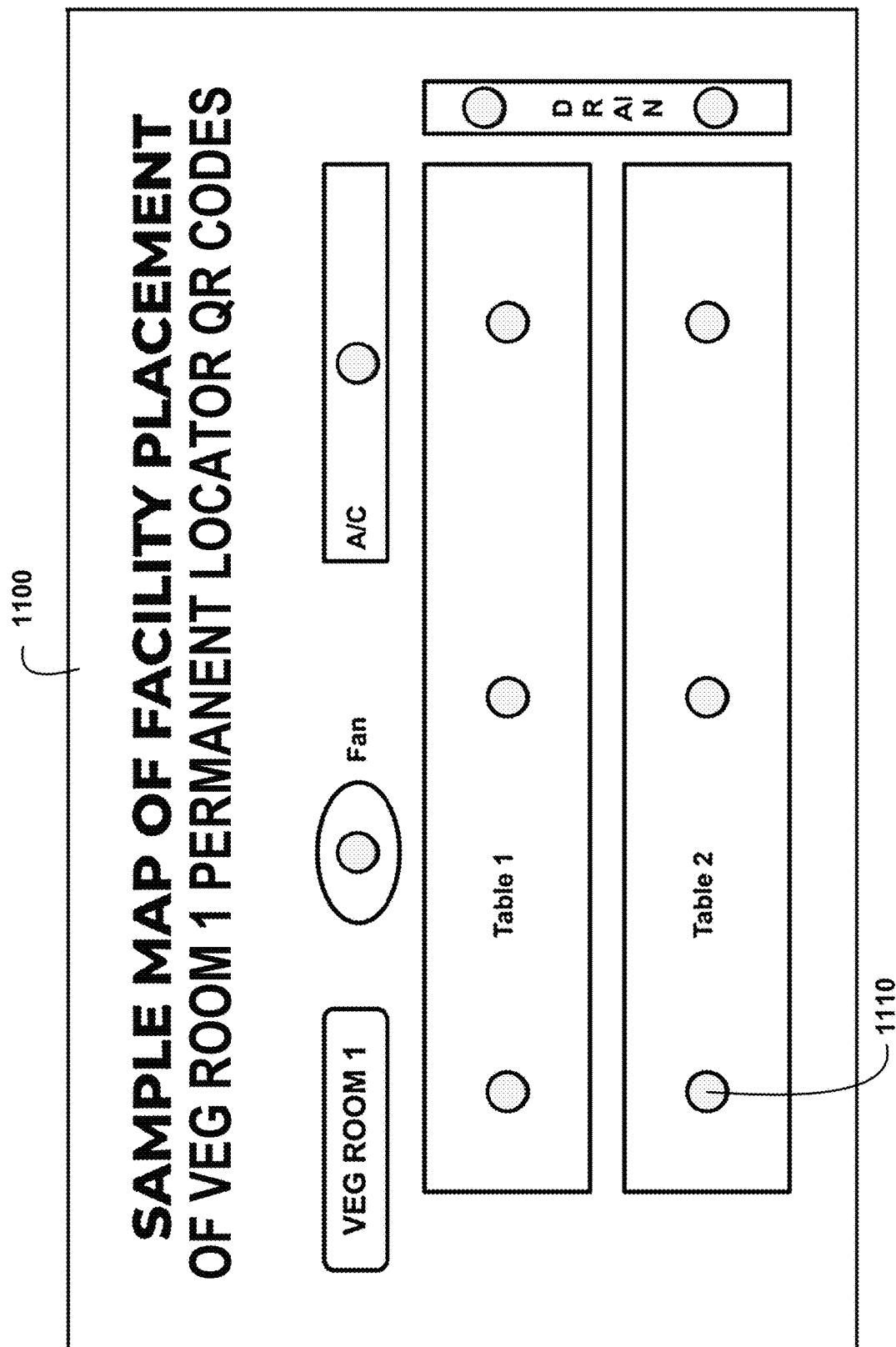
FIG. 11 shows for illustrative purposes only an example of a sample map of veg room 1 facility placement of permanent QR codes of one embodiment.

A sample map of the placement of veg Room 1 Permanent QR Codes:

FIG. 11 shows for illustrative purposes only an example of a sample map of veg room 1 facility placement of veg room 1 permanent QR codes of one embodiment. FIG. 11 shows a sample map of the facility placement of veg room 1 permanent QR code 1100. The veg room 1 facility placement of permanent QR codes 1110 provides uniformity in QR code 1110 placements, which allows the facility and customer to save time searching for the QR code 1110 and facilitates any photos needed to identify the equipment and contents of one embodiment.

Figure 12:
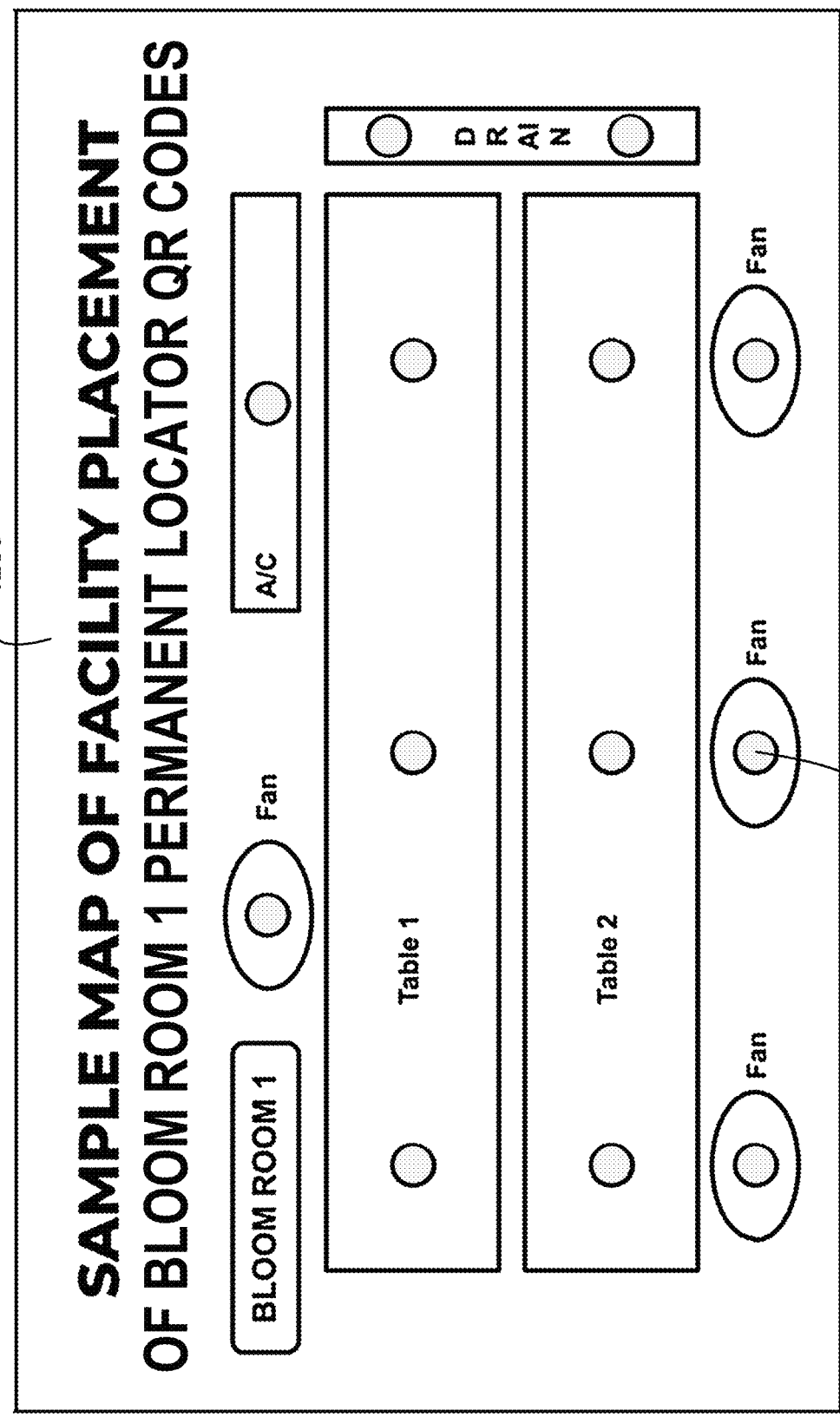
FIG. 12 shows for illustrative purposes only an example of a sample map of bloom room 1 facility placement of permanent QR codes of one embodiment.

A Sample Map of Bloom Room 1 Facility Placement of Permanent Locator QR Codes:

FIG. 12 shows for illustrative purposes only an example of a sample map of bloom room 1 facility placement of permanent QR codes of one embodiment. FIG. 12 shows a sample map of facility placement of bloom room 1 permanent locator QR codes 1200. The predetermined placement of permanent locator QR codes 1210 provides uniformity in QR code 1210 placements which allows the facility and customer to save time searching for the QR code 1210 and facilitates any photos needed to identify the equipment and contents. In this instance, the three fans are needed to refresh the air for the maintenance of the conditions for the blooms of one embodiment.

Figure 13:
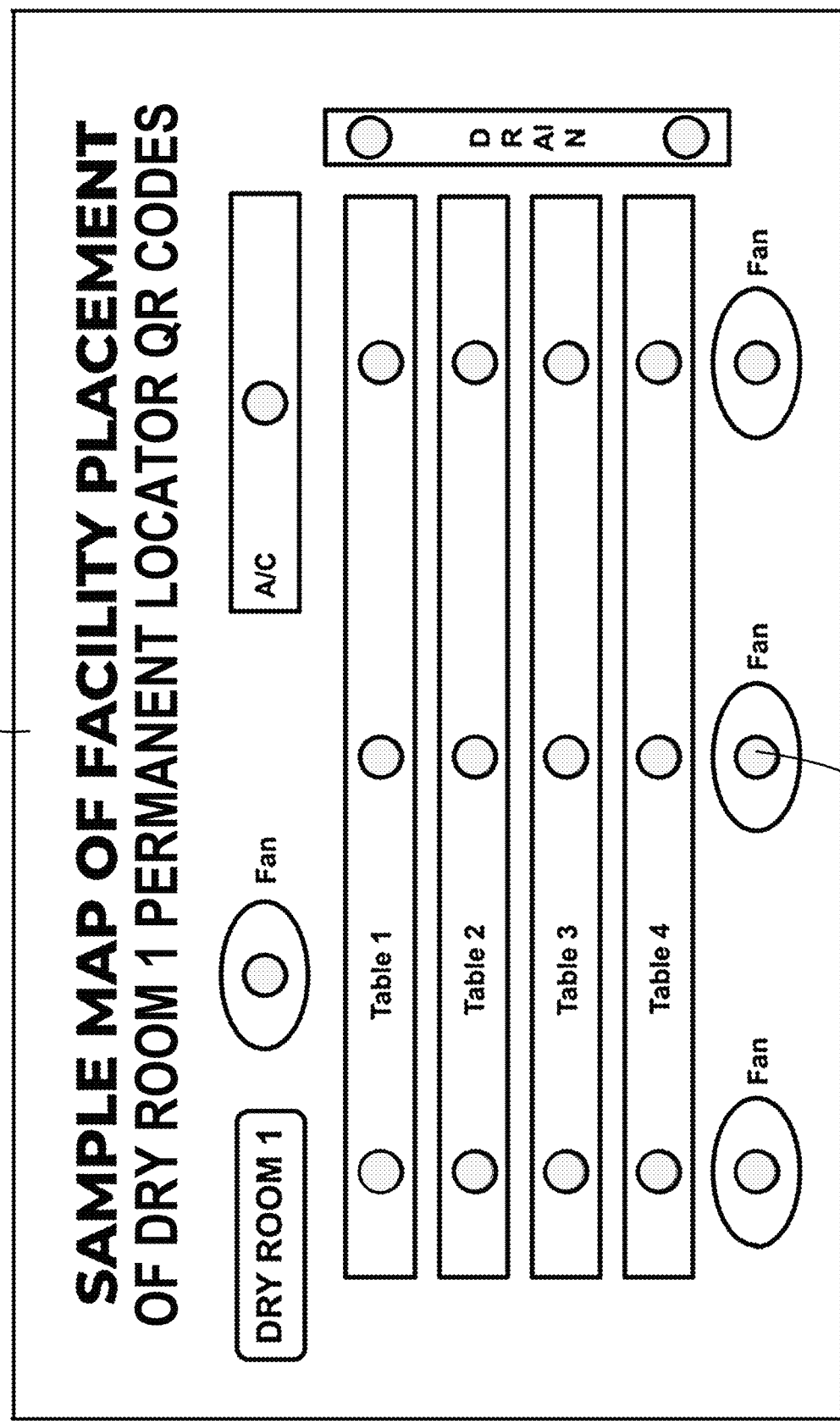
FIG. 13 shows for illustrative purposes only an example of a sample map of dry room 1 facility placement of permanent QR codes of one embodiment.

A Sample Map of Dry Room 1 Facility Permanent Locator QR Codes:

FIG. 13 shows for illustrative purposes only an example of a sample map of dry room 1 facility placement of permanent QR codes of one embodiment. FIG. 13 shows a sample map of the dry room 1 facility placement of dry room 1 permanent QR codes 1300. The predetermined placement of permanent QR codes 1310 provides uniformity in QR code 1310 placements which allows the facility and customer to save time searching for the QR code 1310 and facilitates any photos needed to identify the equipment and contents. In this instance, the four tables need ease in identifying to prevent mismatching contents of the table during the drying processes of one embodiment.

Figure 14:
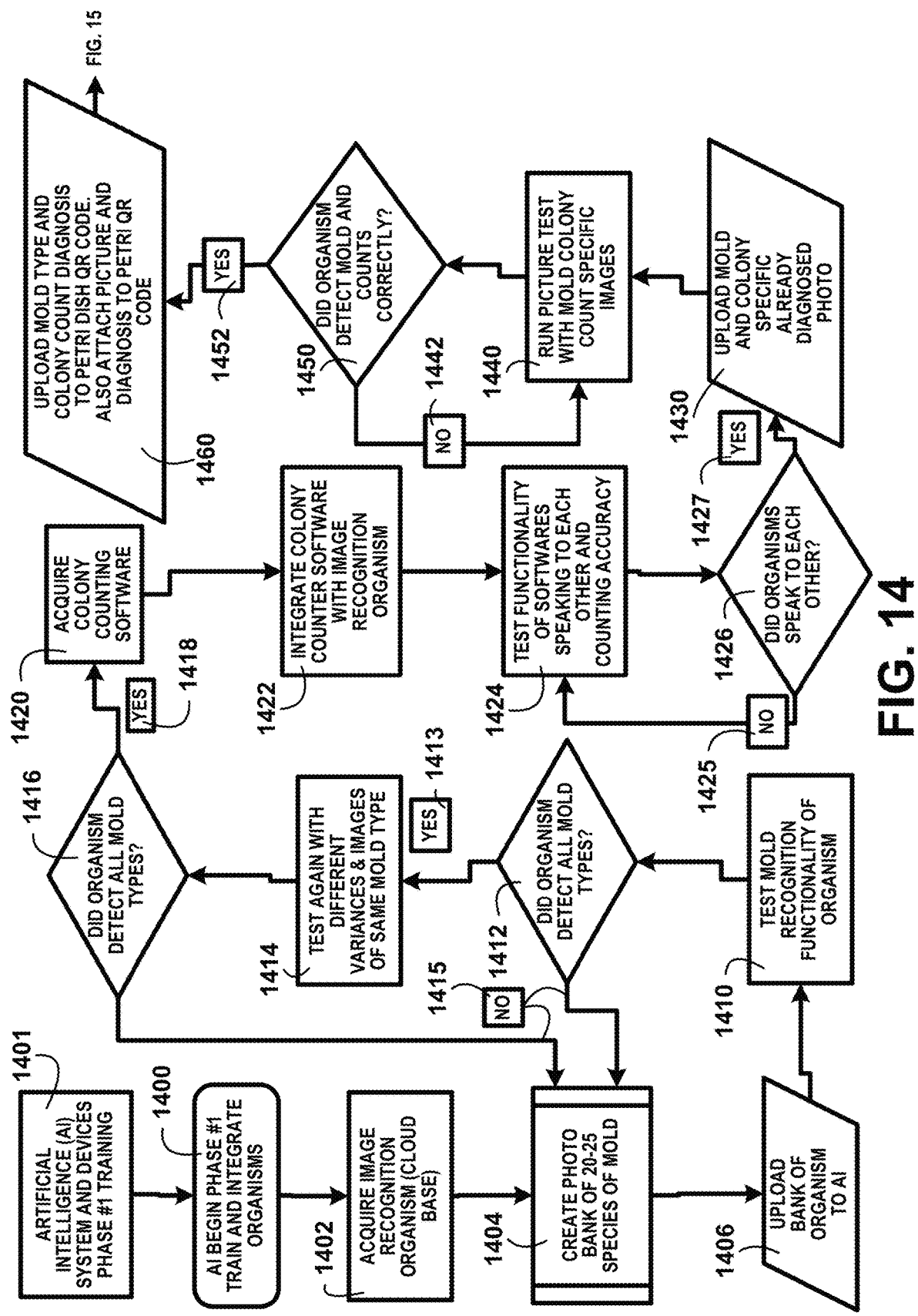
FIG. 14 shows a block diagram of an overview of AI begin phase #1—train and integrate organisms of one embodiment.

AI Begin Phase #1:

FIG. 14 shows for illustrative purposes only an example of AI beginning phase #1-train and integrate organisms of one embodiment. FIG. 14 shows a process for artificial intelligence (AI) system and devices phase #1 training 1401 to train the artificial intelligence device, the testing process, parameters, and results determinations. AI begins phase #1 1400 trains and integrates organisms 1400 to acquire image recognition organism (cloud base) 1402. Create a photo bank of 20-25 species of mold 1404 and upload the bank of organisms to AI 1406. Test mold recognition functionality of organism 1410.

Determination of results is made with questions, for example, Did the organism detect all mold types? 1412. A yes 1413 proceeds to test again with different variances & images of the same mold type 1414. A no 1415 determination returns to create a photo bank of 20-25 species of mold 1404 and upload the bank of organisms to AI 1406. The next training step includes, Did the organism detect all mold types? 1416. A no 1415 determination returns to create a photo bank of 20-25 species of mold 1404.

A yes 1418 results in a process to acquire colony counting software 1420 within the AI device. The training continues to integrate colony counter software with image recognition organism 1422 to test the functionality of software speaking to each other and counting accuracy 1424. Determination of results is made with questions, for example, Did organisms speak to each other? 1426. A no 1425 results returns to the test functionality of software speaking to each other and counting accuracy 1424. A yes 1427 result proceeds to upload mold and colony-specific already diagnosed photo 1430.

The process proceeds to run a picture test with mold colony counting specific images 1440. The results query, for example, Did the organism detect mold and counts correctly? 1450. A no 1442 response returns to repeat the run picture test with mold colony count specific images 1440. A yes 1452 response proceeds to upload mold type and colony count diagnosis to the petri dish QR code, also attach picture and diagnosis to petri QR code 1460. The training process descriptions continue in FIG. 15 of one embodiment.

Figure 15:
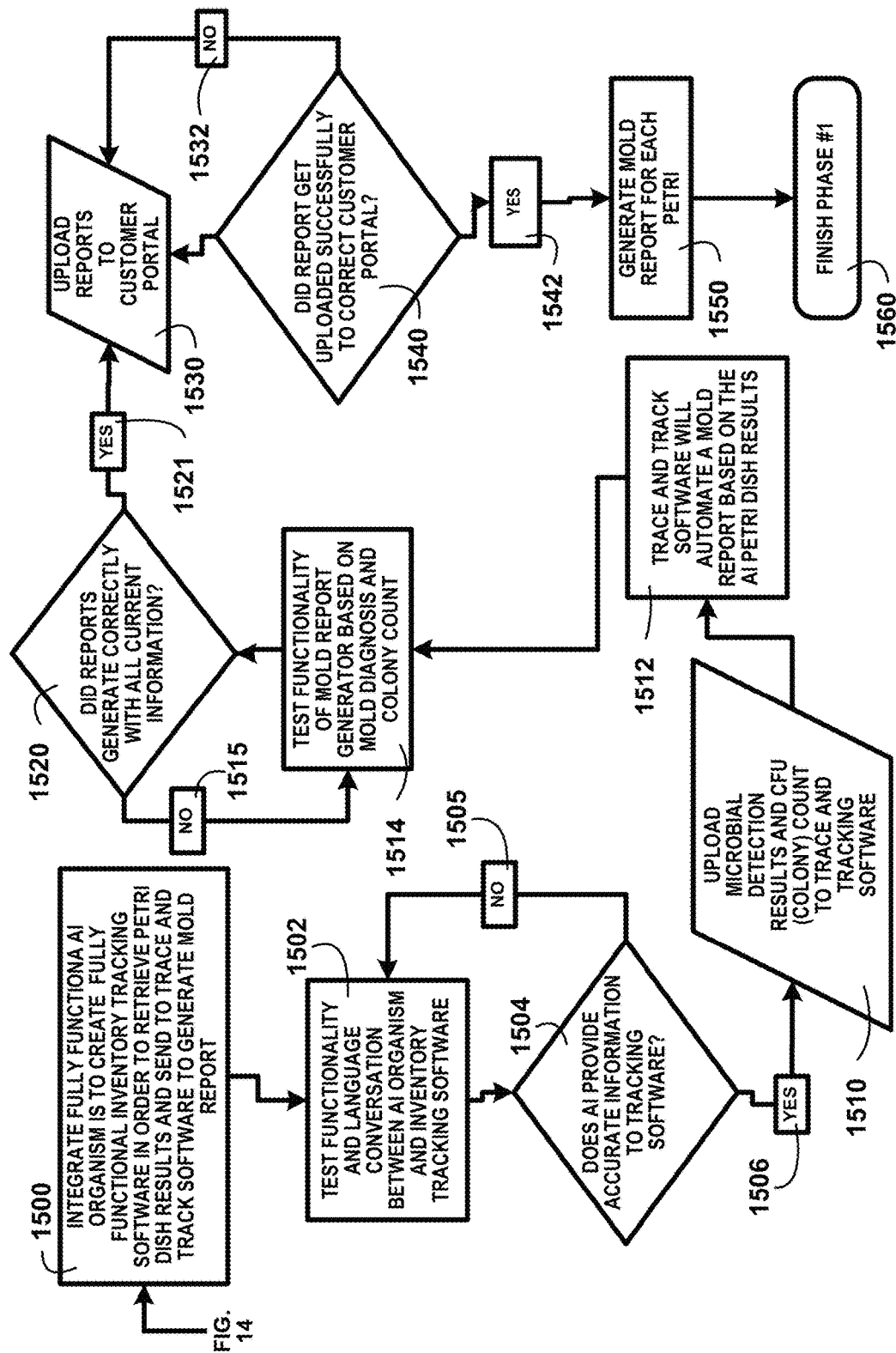
FIG. 15 shows a block diagram of an overview of the integrated fully functional AI organism of one embodiment.

Integrate Fully Functional AI Organism:

FIG. 15 shows for illustrative purposes only an example of integrating fully functional AI organism of one embodiment. FIG. 15 shows a continuation from FIG. 14 of an example of an integrated fully functional AI organism. The process to integrate fully functional AI organisms is to create fully functional inventory tracking software to retrieve petri dish results and send to trace and track software to generate mold report 1500. The process includes testing functionality and language conversation between AI organism and inventory tracking software 1502.

A determination of the results is made with the question, does AI provide accurate information to tracking software? 1504. A no 1505 result returns the process to test functionality and language conversation between AI organism and inventory tracking software 1502. A yes 1506 result continues the process of uploading microbial detection results and CFU (colony) count to trace and tracking software 1510. A trace and track software will automate a mold report based on the AI petri dish results 1512 to test the functionality of the mold report generator based on mold diagnosis and colony count 1514. The test results are reviewed with the question, "Did reports generate correctly with all current information?" 1520. A no 1515 response returns the process to test the functionality of the mold report generator based on mold diagnosis and colony count 1514.

A yes 1521 response continues to upload reports to customer portal 1530. The results are determined with the question, did the report get uploaded successfully to the correct customer portal? 1540. A no 1532 answer returns the process to upload reports to customer portal 1530. A yes 1542 answer continues to generate a mold report for each petri 1550 dish tested to finish phase #1 1560 of the AI training of one embodiment.

Figure 16:
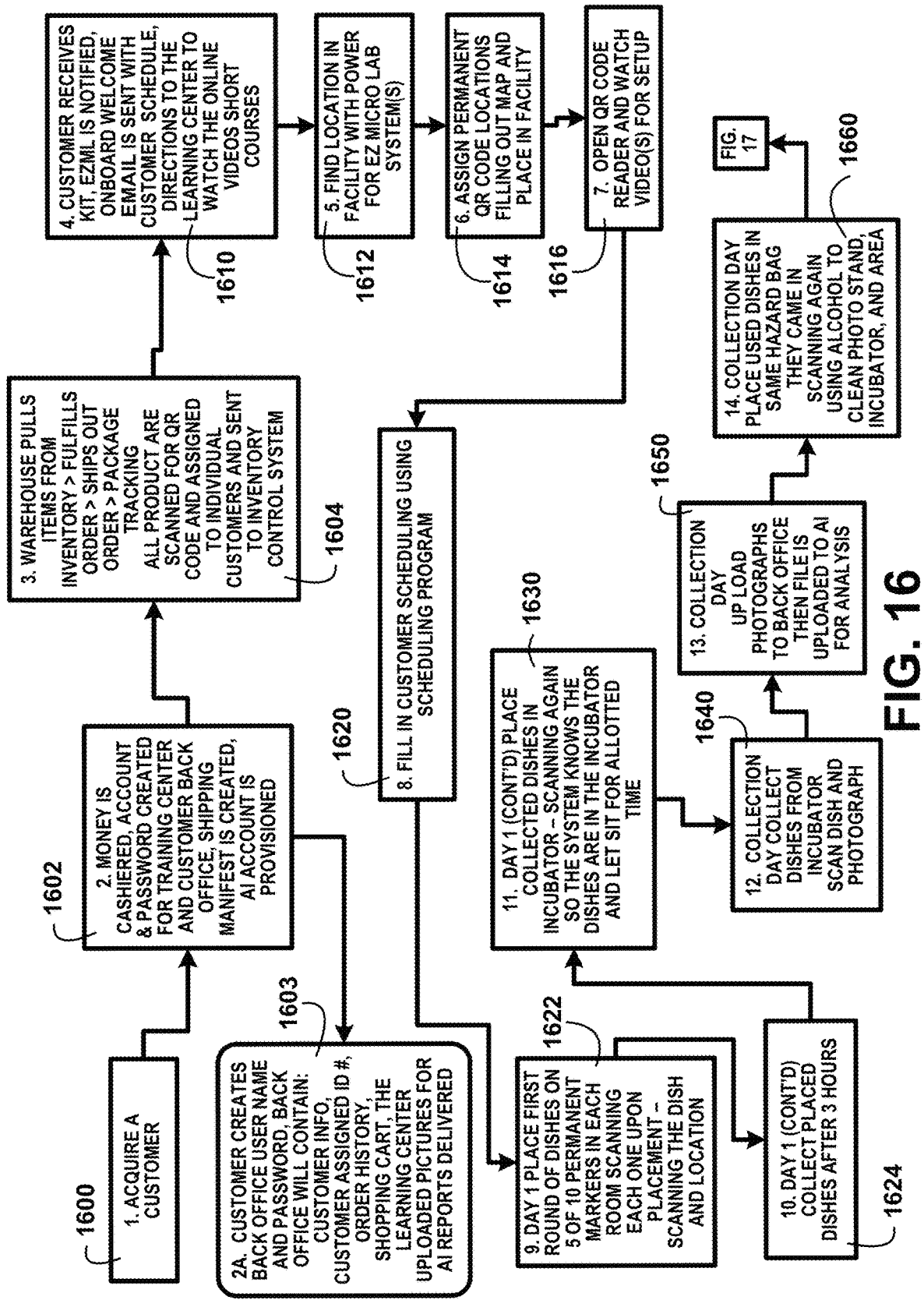
FIG. 16 shows a block diagram of an overview of an acquired customer of one embodiment.

Acquire Customer:

FIG. 16 shows for illustrative purposes only an example of an acquired customer of one embodiment. FIG. 16 shows the steps to 1. acquire a customer 1600. Step 2. Money is cashiered, an account & password are created for a training center and customer back office, a shipping manifest is created, AI account is provisioned 1602. The customer then follows step 2a. customer creates a back-office username and password, the back office will contain: customer information, customer assigned ID #, order history, shopping cart, and the learning center uploaded pictures for AI reports delivered 1603. The acquisition continues with step 3. warehouse pulls items from inventory>fulfills order>ships out order>package tracking all products are scanned for QR code assigned to individual customers and sent to inventory control system 1604. Step 4. The customer receives the kit, EZML is notified, an onboard welcome email is sent with the customer schedule, and directions to the learning center to watch the online videos short courses 1610.

The customer then will follow step 5. find a location in a facility with power for EZ micro lab system(s) 1612 and as directed in step 6. assign permanent QR code locations fill out the map and place in facility 1614. The instructions include customer action in step 7. open the QR code reader and watch video(s) for setup 1616. Step 8. fill in customer scheduling using scheduling program 1620. The instructions continue with 9. day 1 place the first round of dishes on 5 of 10 permanent markers in each room scanning each one upon placement-scanning the dish and location 1622. 10. day 1 (cont'd) collect placed dishes after 3 hours 1624. 11. day 1 (cont'd) place collected dishes in the incubator-scanning again so the system knows the dishes are in the incubator and let sit for the allotted time 1630. The schedule continues with 12. collection day collect dishes from the incubator scan dish and photograph 1640. Continuing 13. collection day upload photographs to the back office then the file is uploaded to AI for analysis 1650. Continuing 14. collection day place used dishes in the same hazard bag they came in scanning again using alcohol to clean the photo stand, incubator, and area 1660. The scheduling descriptions continue in FIG. 17 of one embodiment.

Figure 17:
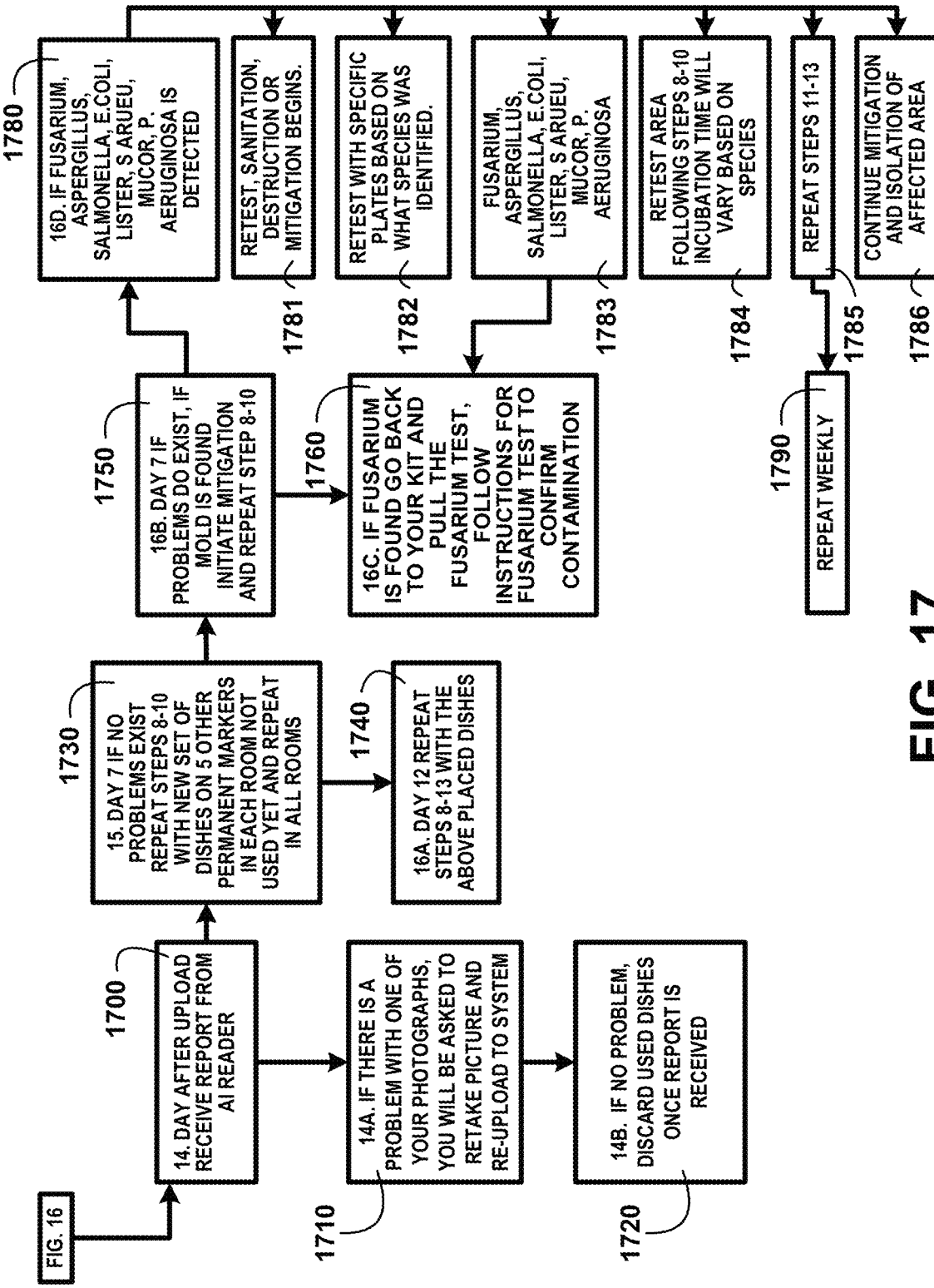
FIG. 17 shows a block diagram of an overview of the received report from AI reader of one embodiment.

Receive Report from AI Reader:

FIG. 17 shows for illustrative purposes only an example of a received report from AI reader of one embodiment. FIG. 17 shows a continuation from FIG. 16. Step 14 continues with 14. day after upload receive report from AI reader 1700. 14a. If there is a problem with one of your photographs, you will be asked to retake the picture and re-upload it to system 1710. 14B. if no problem, discard used dishes once the report is received 1720. 15. Day 7 if no problems exist repeat steps 8-10 with a new set of dishes on 5 other permanent markers in each room not used yet and repeat in all rooms 1730.

16a. day 12 repeat steps 8-13 with the above-placed dishes 1740. 16b. day 7 if problems do exist and if mold is found initiate mitigation and repeat steps 8-10 1750. 16c. If the *Fusarium* is found go back to your kit and pull the *Fusarium* test, follow the instructions for the *Fusarium* test to confirm contamination 1760. 16d. if *Fusarium, Aspergillus, Salmonella, E. coli, Lister, S Arueu, Mucor, P. Aeruginosa* is detected 1780; retest, sanitation, destruction, or mitigation begins 1781.

Retest with specific plates based on what species was identified 1782. The species identified include *Fusarium, Aspergillus, Salmonella, E. coli, Lister, S Arueu, Mucor, P. Aeruginosa* 1783. 16c. If *Fusarium* is found go back to your kit and pull the *Fusarium* test, follow the instructions for the *Fusarium* test to confirm contamination 1760. Retest area following steps 8-10, incubation time will vary based on species 1784. Repeat steps 11-13 1785 and repeat weekly 1790. Continue mitigation and isolation of affected area 1786 of one embodiment.

Figure 18:
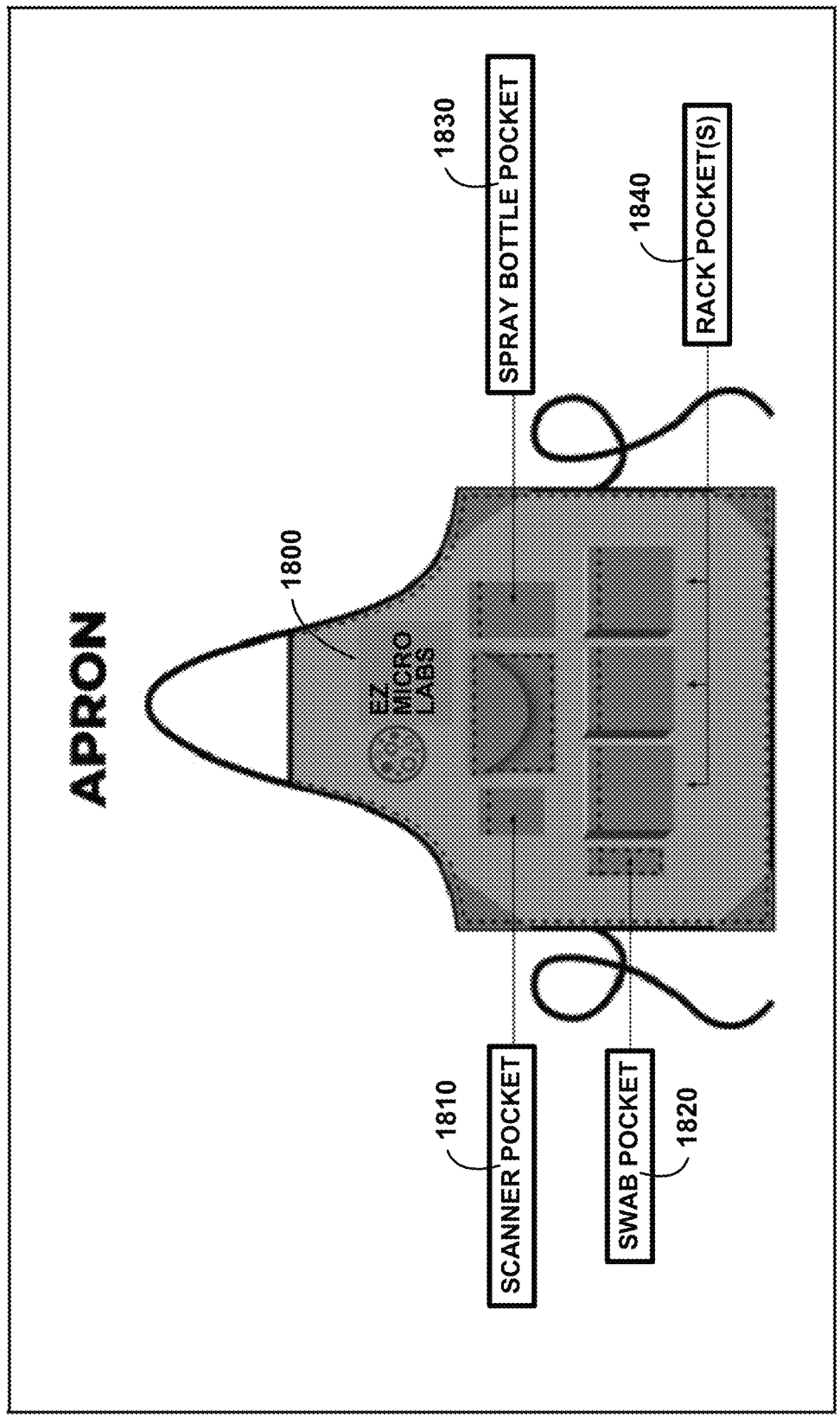
FIG. 18 shows for illustrative purposes only an example of a utility apron of one embodiment.

Utility Apron:

FIG. 18 shows for illustrative purposes only an example of a utility apron of one embodiment. FIG. 18 shows a utility apron 1800 that is included in the Kit. The utility apron 1800 includes a scanner pocket 1810, swab pocket 1820, spray bottle pocket 1830, and rack pocket(s) 1840 to allow the user to carry the tools to carry out the testing processes of one embodiment.

Figure 19A:
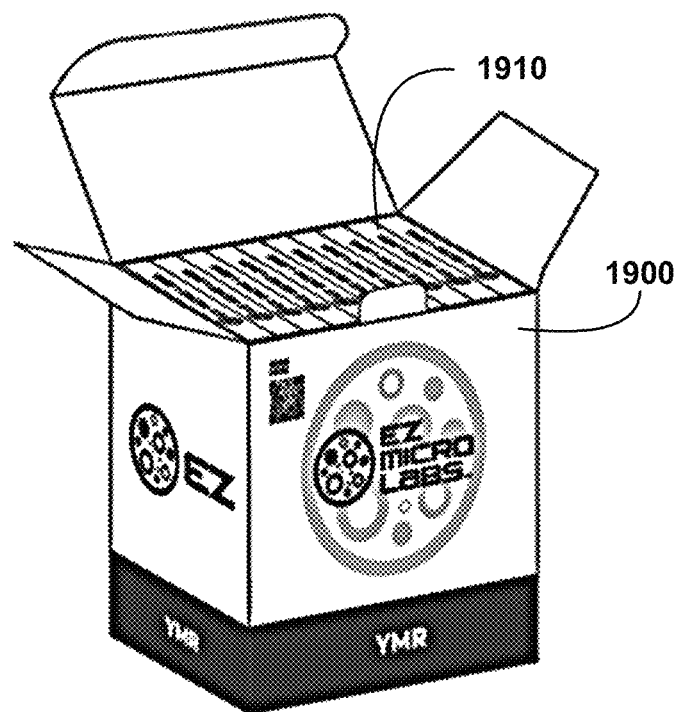
FIG. 19A shows for illustrative purposes only an example of a YMR bio-insert rack open utility apron of one embodiment.

YMR Bio-Insert Rack Open:

FIG. 19A shows for illustrative purposes only an example of a YMR bio-insert rack open of one embodiment. FIG. 19A shows YMR bio-insert rack-open 1900. Through the opening are seen racks 1910 used in the test processing. Yeast/Mold Rapid (YMR) is a test method to detect mold and yeast of one embodiment.

Figure 19B:
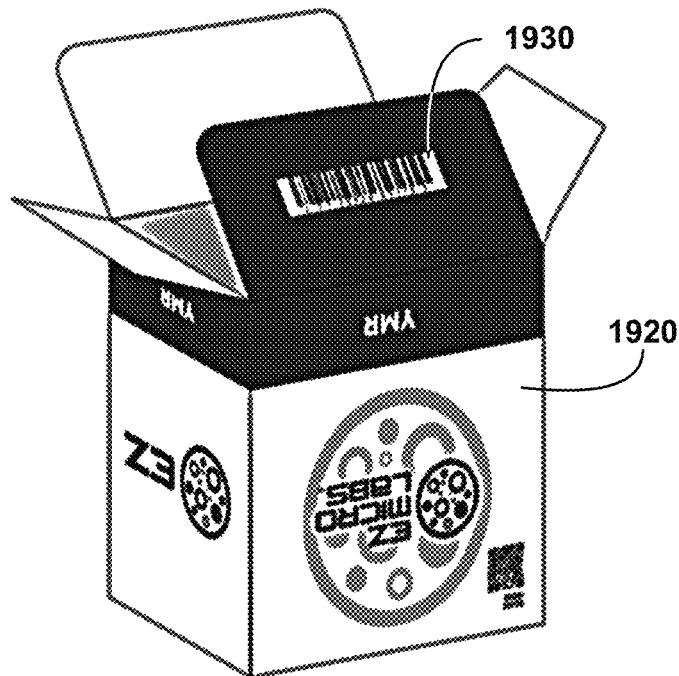
FIG. 19B shows for illustrative purposes only an example of a YMR bio-insert rack bottom of one embodiment.

YMR Bio-Insert Rack Bottom:

FIG. 19B shows for illustrative purposes only an example of a YMR bio-insert rack bottom of one embodiment. FIG. 19B shows a YMR bio-insert rack-bottom 1920 that includes an identifying barcode 1930 of one embodiment.

Figure 20:
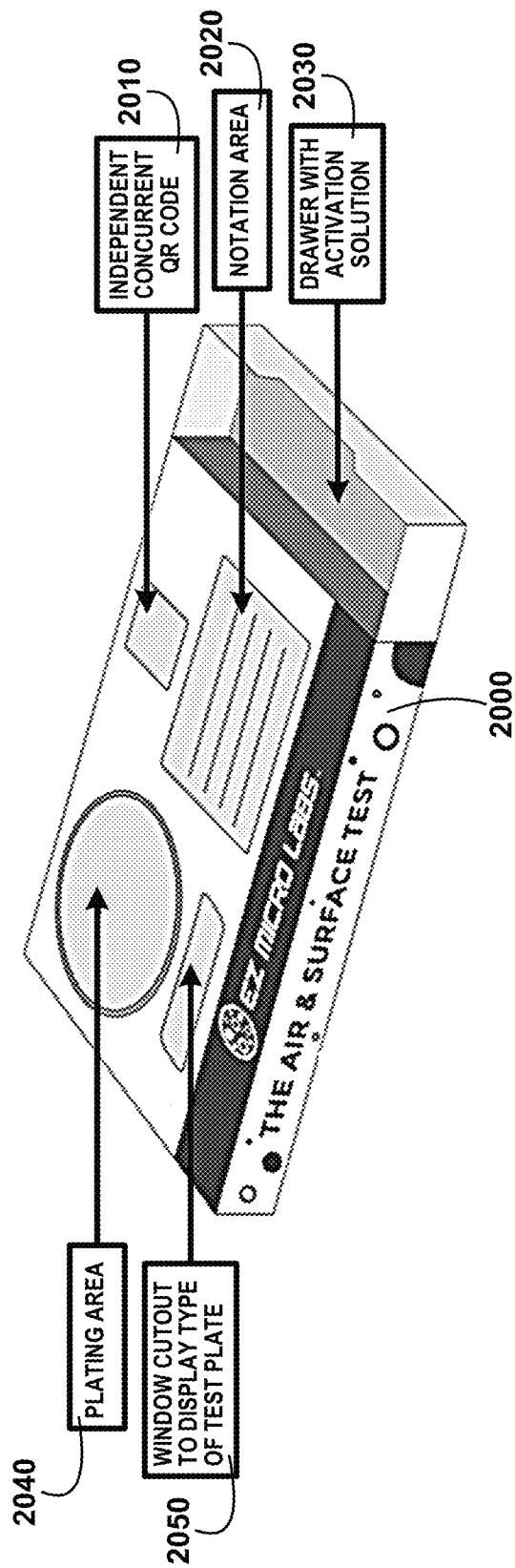
FIG. 20 shows for illustrative purposes only an example of an air and surface test of one embodiment.

Air and Surface Test:

FIG. 20 shows for illustrative purposes only an example of an air and surface test of one embodiment. FIG. 20 shows the air & surface test 2000 in a container marked with an independent concurrent QR code 2010. The air & surface test 2000 in a container shows a notation area 2020, a drawer with activation solution 2030, a plating area 2040, and a window cutout to display the type of test plate 2050 of one embodiment.

Figure 21B:
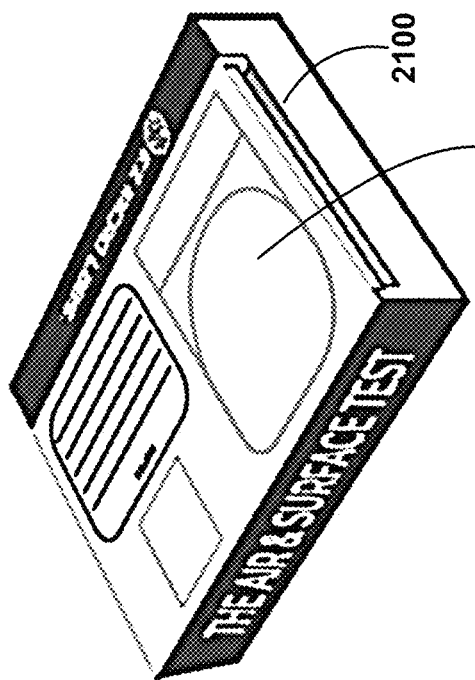
FIG. 21B shows for illustrative purposes only an example of an air and surface test front view closed of one embodiment.
Figure 21C:
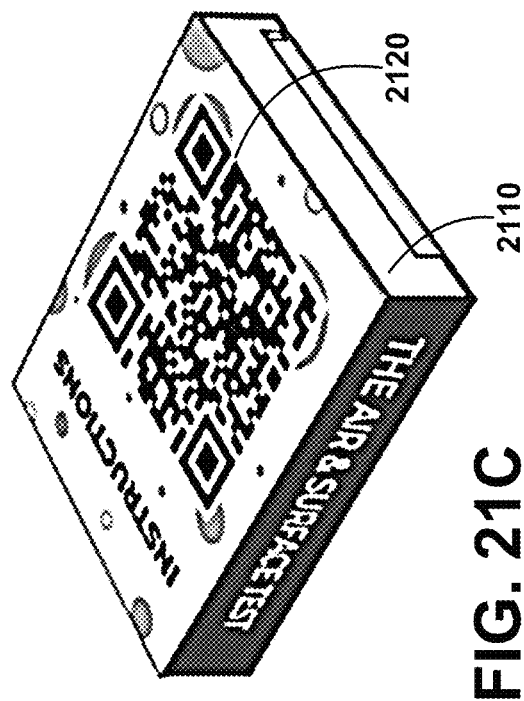
FIG. 21C shows for illustrative purposes only an example of an air and surface test back-bottom view of one embodiment.
Figure 21A:
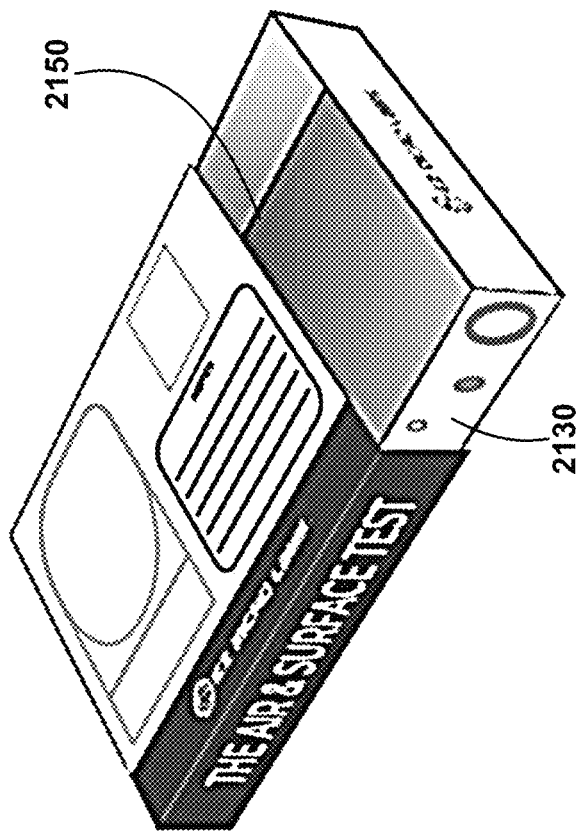
FIG. 21A shows for illustrative purposes only an example of an air and surface test front view open of one embodiment.

Air and Surface Test Front View Open:

FIG. 21A shows for illustrative purposes only an example of an air and surface test front view open of one embodiment. FIG. 21A shows an open test kit 2130 revealing the plant material drawer 2150 of one embodiment.

Air and Surface Test Front View Closed:

FIG. 21B shows for illustrative purposes only an example of an air and surface test front view closed of one embodiment. FIG. 21B shows the air & surface test top 2100 that includes a plating area 2040 of one embodiment.

Air and Surface Test Back-Bottom View:

FIG. 21C shows for illustrative purposes only an example of an air and surface test back-bottom view of one embodiment. FIG. 21C shows the air & surface test bottom 2110 which includes a QR code 2120 for identification of one embodiment.

Figure 22:
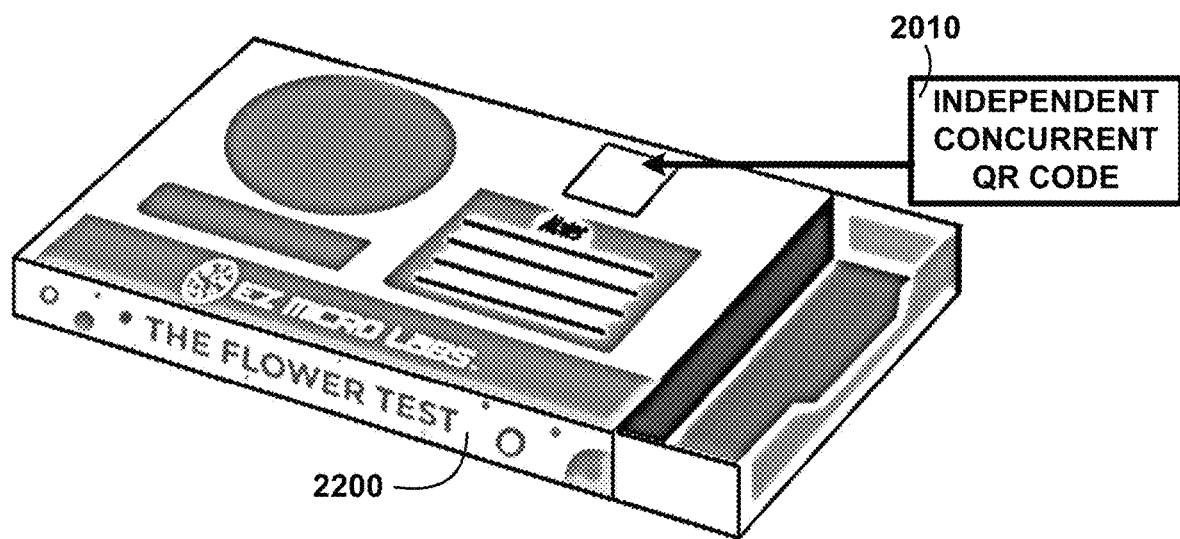
FIG. 22 shows for illustrative purposes only an example of a Flower Test Bio-Insert-Open of one embodiment.

Flower Test Bio-Insert-Open:

FIG. 22 shows for illustrative purposes only an example of a Flower Test Bio-Insert-Open of one embodiment. FIG. 22 shows the flower test 2200 independent concurrent QR code 2010 used to identify the particular test of one embodiment.

Figure 23A:
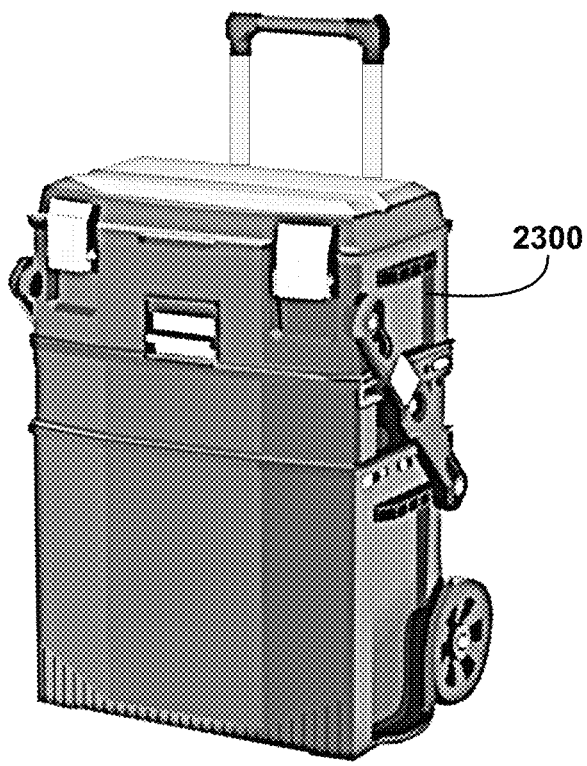
FIG. 23A shows for illustrative purposes only an example of a Mobile Tool Station of one embodiment.

Mobile Tool Station:

FIG. 23A shows for illustrative purposes only an example of a Mobile Tool Station of one embodiment. FIG. 23A shows a mobile tool station 2300 used to carry the tools the user uses during the testing processes of one embodiment.

Figure 23B:
FIG. 23B shows for illustrative purposes only an example of a Mobile Tool Station Opened of one embodiment.

Mobile Tool Station Opened:

FIG. 23B shows for illustrative purposes only an example of a Mobile Tool Station Opened of one embodiment. FIG. 23B shows a mobile tool station opened 2302 showing the tools the user uses during the testing processes of one embodiment.

Figure 23C:
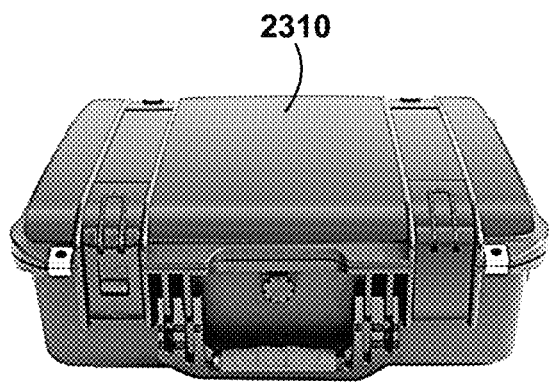
FIG. 23C shows for illustrative purposes only an example of a Mobile Carrying Case of one embodiment.

Mobile Carrying Case:

FIG. 23C shows for illustrative purposes only an example of a Mobile Carrying Case of one embodiment. FIG. 23C shows a mobile carrying case 2310 that allows the user to carry tools and supplies from, for example, one room to another room for testing of one embodiment.

Figure 23D:
FIG. 23D shows for illustrative purposes only an example of a Mobile Carrying Case Opened of one embodiment.

Mobile Carrying Case Opened:

FIG. 23D shows for illustrative purposes only an example of a Mobile Carrying Case Opened of one embodiment. FIG. 23C shows a mobile carrying case opened 2312 showing the user tools and supplies available to the user from, for example, one room to another room for testing of one embodiment.

Figure 24A:
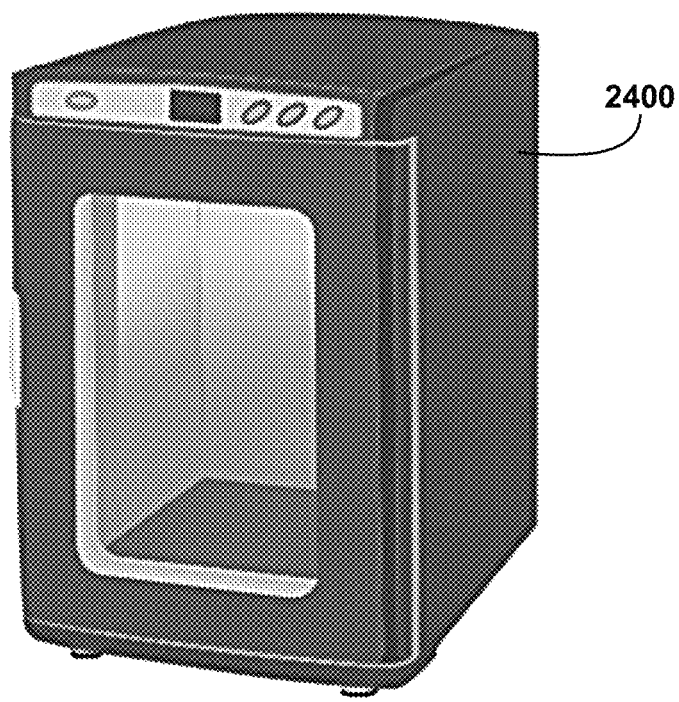
FIG. 24A shows for illustrative purposes only an example of an Incubator front perspective view of one embodiment.

Incubator Front Perspective View:

FIG. 24A shows for illustrative purposes only an example of an Incubator front perspective view of one embodiment. FIG. 24A shows incubator front view 2400. The front door includes a glass window allowing the user to check the testing materials without having to open the door and interrupt the incubation process of one embodiment.

Figure 24B:
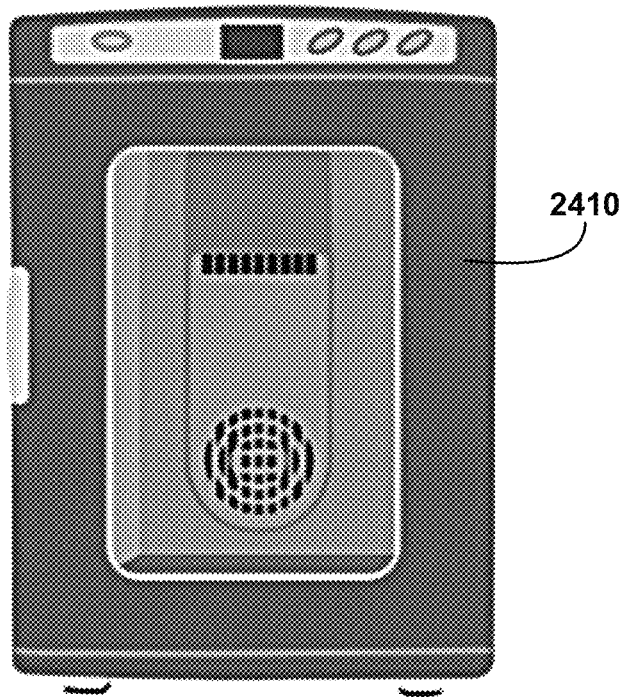
FIG. 24B shows for illustrative purposes only an example of an Incubator back view of one embodiment.

Incubator Back View:

FIG. 24B shows for illustrative purposes only an example of an Incubator back view of one embodiment. FIG. 24B shows incubator back view 2410 showing the exhaust ventilation screen and the heater elements of one embodiment.

Figure 25A:
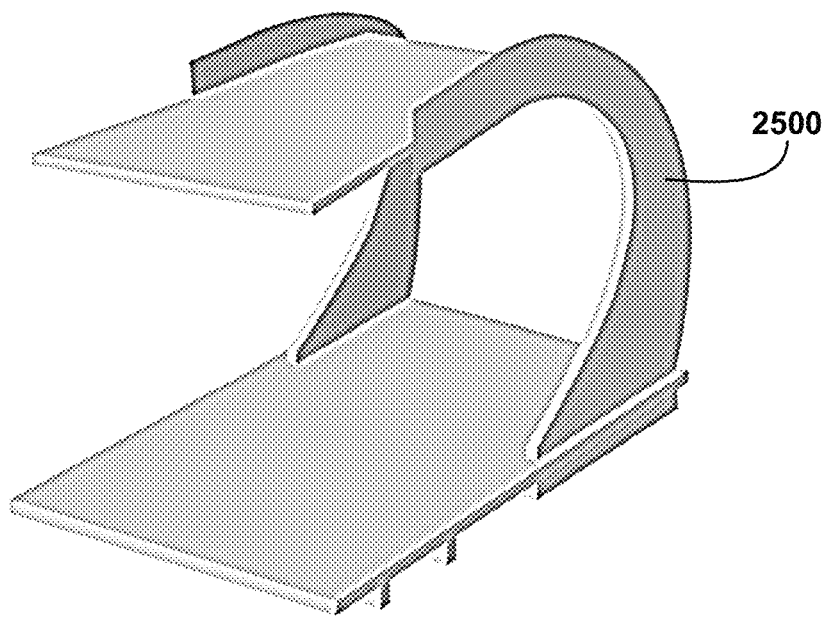
FIG. 25A shows for illustrative purposes only an example of a Photo Stand of one embodiment.

Photo Stand:

FIG. 25A shows for illustrative purposes only an example of a photo stand of one embodiment. FIG. 25A shows an EZ photo stand 2500 used to mount a camera to photograph plant materials used in the processing to detect the presence of mold. The photograph is sent to an artificial intelligence (AI) device. The AI device reads the dish and sends the results (mold ID and CFU count back to the reporting system for display of one embodiment.

Figure 25B:
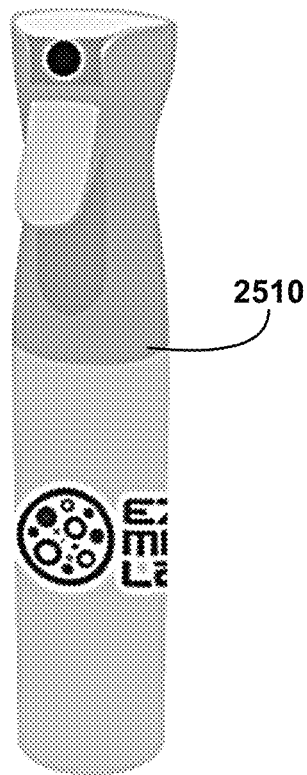
FIG. 25B shows for illustrative purposes only an example of an Isopropyl Spray Bottle of one embodiment.

Isopropyl Spray Bottle:

FIG. 25B shows for illustrative purposes only an example of an Isopropyl Spray Bottle of one embodiment. FIG. 25B shows an isopropyl spray bottle 2510 used to apply alcohol for cleansing tools of any mold acquired during contact with the plant materials of one embodiment.

Figure 26A:
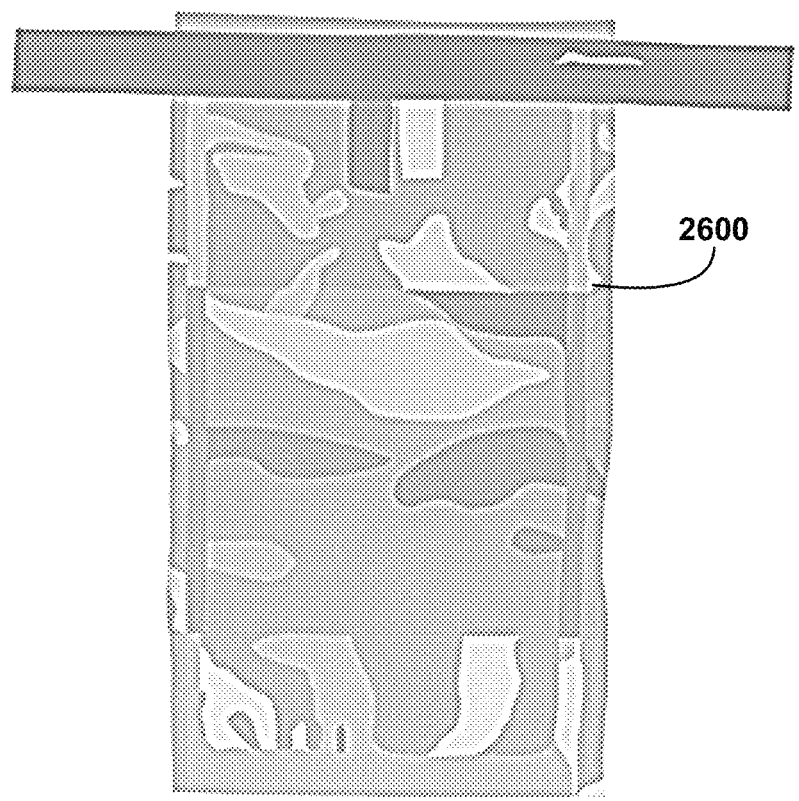
FIG. 26A shows for illustrative purposes only an example of a Sterile Blended Bag of one embodiment.

Sterile Blended Bag:

FIG. 26A shows for illustrative purposes only an example of a Sterile Blended Bag of one embodiment. FIG. 26A shows a sterile blended bag 2600 used to store plant materials during the testing processes of one embodiment.

Figure 26B:
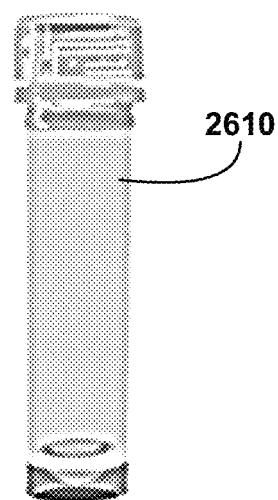
FIG. 26B shows for illustrative purposes only an example of a Buffer Solution of one embodiment.

YMR Activating Solution:

FIG. 26B shows for illustrative purposes only an example of a YMR Activating Solution of one embodiment. FIG. 26B shows YMR activating solution 2610 used to apply to plant materials to detect mold of one embodiment Buffer Solution(s):

FIG. 27A shows for illustrative purposes only an example of a buffer solution(s) of one embodiment. FIG. 27A shows a buffer solution(s) 2700 used in the testing process of one embodiment.

Buffer B Solution:

FIG. 27B shows for illustrative purposes only an example of a Buffer B Solution of one embodiment. FIG. 27B shows Buffer B 2710 used in the testing process of one embodiment.

Pipette:

FIG. 27C shows for illustrative purposes only an example of a Pipette of one embodiment. FIG. 27C shows a pipette 2720, where pipettes are used for water collecting during the testing processing of one embodiment.

Flower and Plant Material Measuring Scale:

FIG. 27D shows for illustrative purposes only an example of a flower and plant material measuring scale of one embodiment. FIG. 27D shows a flower and plant material measuring scale 2730 used to measure a predetermined weight of flower and plant material to prepare for testing of one embodiment.

Figure 28A:
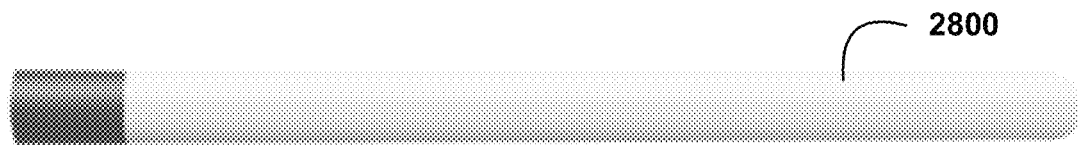
FIG. 28A shows for illustrative purposes only an example of a Sterile Swab of one embodiment.

Sterile Swab:

FIG. 28A shows for illustrative purposes only an example of a Sterile Swab of one embodiment. FIG. 28A shows a sterile swab 2800. Multiple sterile swabs are provided with the testing equipment of one embodiment.

Figure 28B:
FIG. 28B shows for illustrative purposes only an example of a Sterile Swab out of case of one embodiment.

Sterile Swab Out of Case:

FIG. 28B shows for illustrative purposes only an example of a Sterile Swab out of case of one embodiment. FIG. 28B shows a sterile swab 2802 Sterile Swab out of the case. The sterile swabs are used to take test samples of surfaces, for example, shelves, tables, and other surfaces within the facility to detect mold and bacteria infestations. Multiple sterile swabs are provided with the testing equipment of one embodiment.

Figure 28C:
FIG. 28C shows for illustrative purposes only an example of a Forceps of one embodiment.

Forceps:

FIG. 28C shows for illustrative purposes only an example of a Forceps of one embodiment. FIG. 28C shows forceps 2810 used to handle plant materials to prevent physical contact with the user. The forceps 2810 in one embodiment are used to select and place flower and plant materials on the measuring scale 2730 during the Flower Test. The forceps 2810 are cleaned using alcohol between uses to prevent conveying mold from infected plant materials to non-infected plant materials of one embodiment.

Figure 28D:
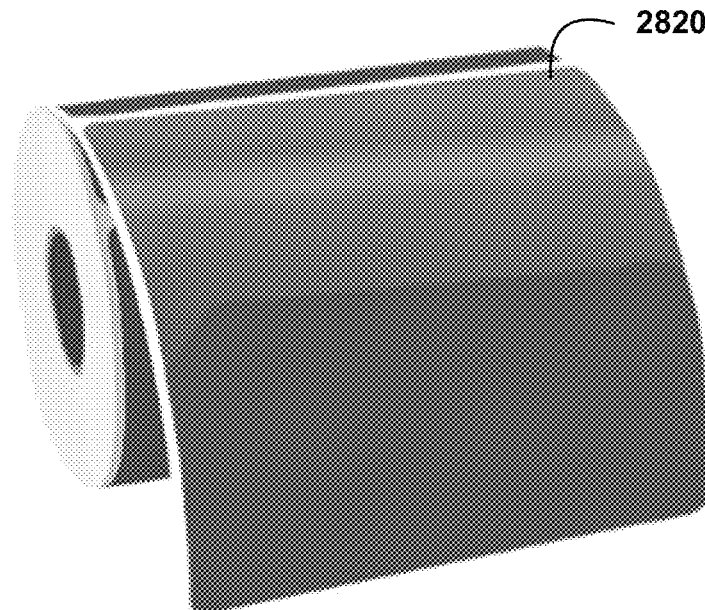
FIG. 28D shows for illustrative purposes only an example of Hazard Stickers of one embodiment.

Hazard Stickers:

FIG. 28D shows for illustrative purposes only an example of Hazard Stickers of one embodiment. FIG. 28D shows hazard stickers 2820 used to seal used test sample. The hazard stickers 2820 identify and alert users of the content of a container with possible infected plant materials of one embodiment.

Figure 29A:
FIG. 29A shows for illustrative purposes only an example of a Permanent Incubator Sticker of one embodiment.

Permanent Incubator Sticker:

FIG. 29A shows for illustrative purposes only an example of a Permanent Incubator Sticker of one embodiment. FIG. 29A shows a permanent incubator sticker 2900 used to identify with a QR code A 2910 plant material containers carrying incubated plant materials of one embodiment.

Figure 29B:
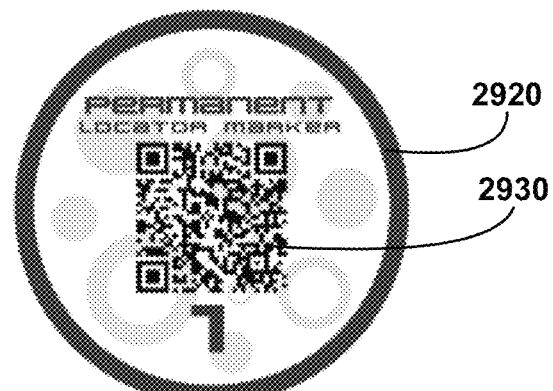
FIG. 29B shows for illustrative purposes only an example of a Permanent Locator Sticker of one embodiment.

Permanent Locator Sticker:

FIG. 29B shows for illustrative purpose only an example of a Permanent Locator Sticker of one embodiment. FIG. 29B shows a permanent locator sticker 2920 identified with a QR code 1 2930. The permanent locator sticker 2920 is used to locate and identify specific groupings of plant materials of one embodiment.

Figure 29C:
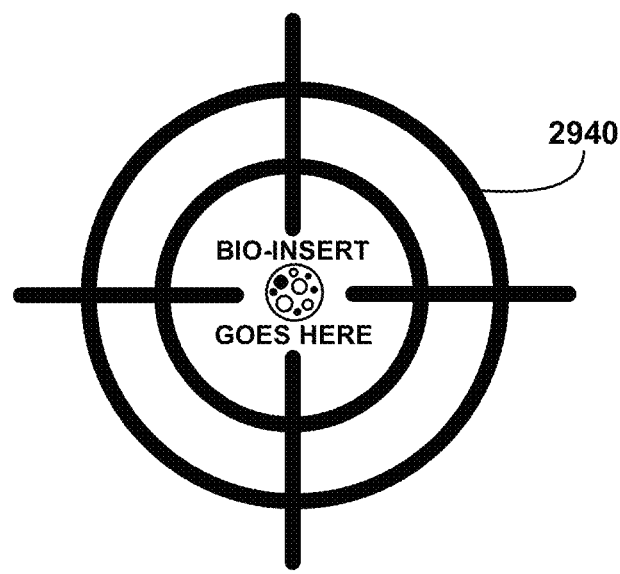
FIG. 29C shows for illustrative purposes only an example of a Target Locator Sticker of one embodiment.

Target Locator Sticker:

FIG. 29C shows for illustrative purpose only an example of a Target Locator Sticker of one embodiment. FIG. 29C shows a Target Locator Sticker 2940 used to locate air testing sites within the facility. A bio-insert is prepared for testing and placed on the Target Locator Sticker 2940 for 2 hours to get exposure to airflow, then prepared for scanning and a network determination of any mold and bacteria infestations of one embodiment.

Figure 30C:
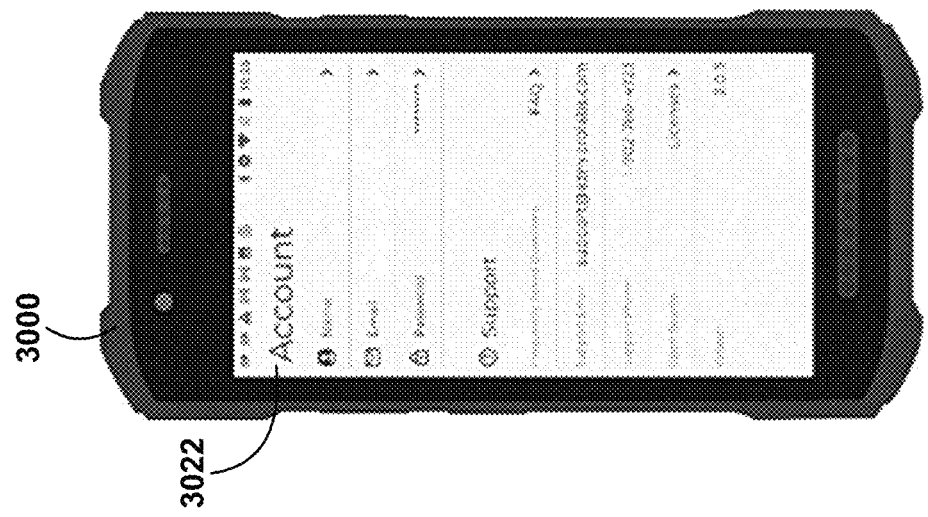
FIG. 30C shows for illustrative purposes only an example of a scanner application in the user account portal section of one embodiment.
Figure 30B:
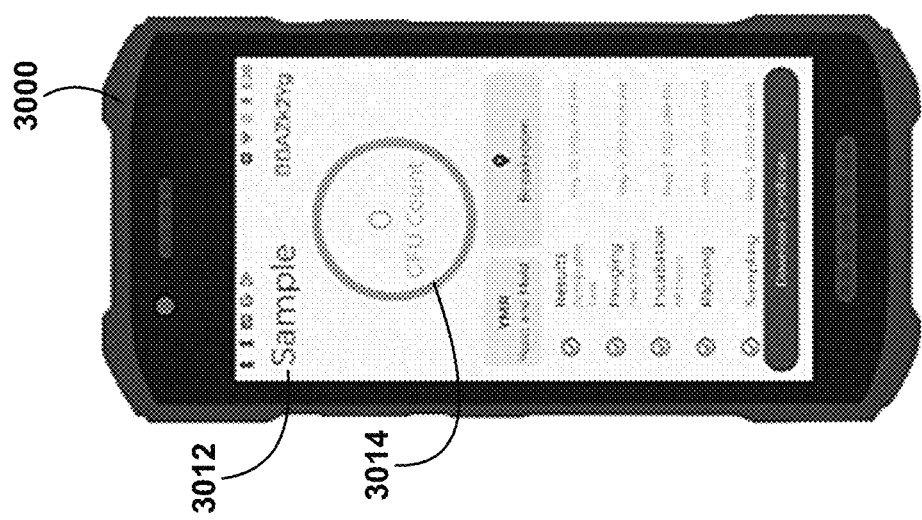
FIG. 30B shows for illustrative purposes only an example of a scanner application in the test sample reporting section of one embodiment.
Figure 30A:
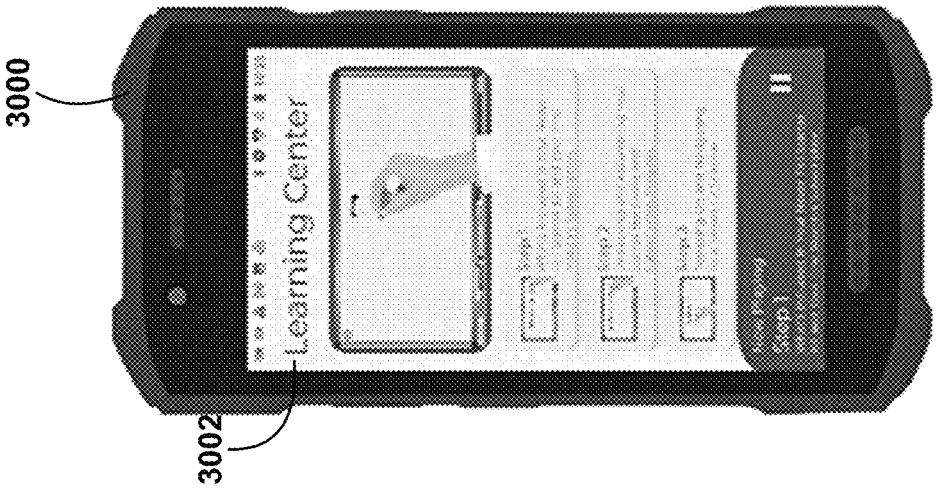
FIG. 30A shows for illustrative purposes only an example of a scanner application in the learning center of one embodiment.

A Scanner Application in the Learning Center:

FIG. 30A shows for illustrative purpose only an example of a scanner application in the learning center of one embodiment. FIG. 30A shows a scanner 3000 having a plant material testing application. In this example, the user has selected the learning center 3002 to view instructions for a particular testing action of one embodiment.

Scanner Application in the Test Sample Reporting Section:

FIG. 30B shows for illustrative purposes only an example of a scanner application in the test sample reporting section of one embodiment. FIG. 30B shows a scanner 3000 having a plant material testing application. In this example, the user has selected the test sample reporting section 3012 to view a unit count 3014 of a test sample of any detected mold and bacteria infestations of one embodiment.

A Scanner Application in the User Account Portal Section:

FIG. 30C shows for illustrative purpose only an example of a scanner application in the user account portal section of one embodiment. FIG. 30C shows a scanner 3000 having a plant material testing application. In this example, the user has selected the user account portal section 3022 to view the user's account, for example, to order additional testing supplies of one embodiment.

Figure 31:
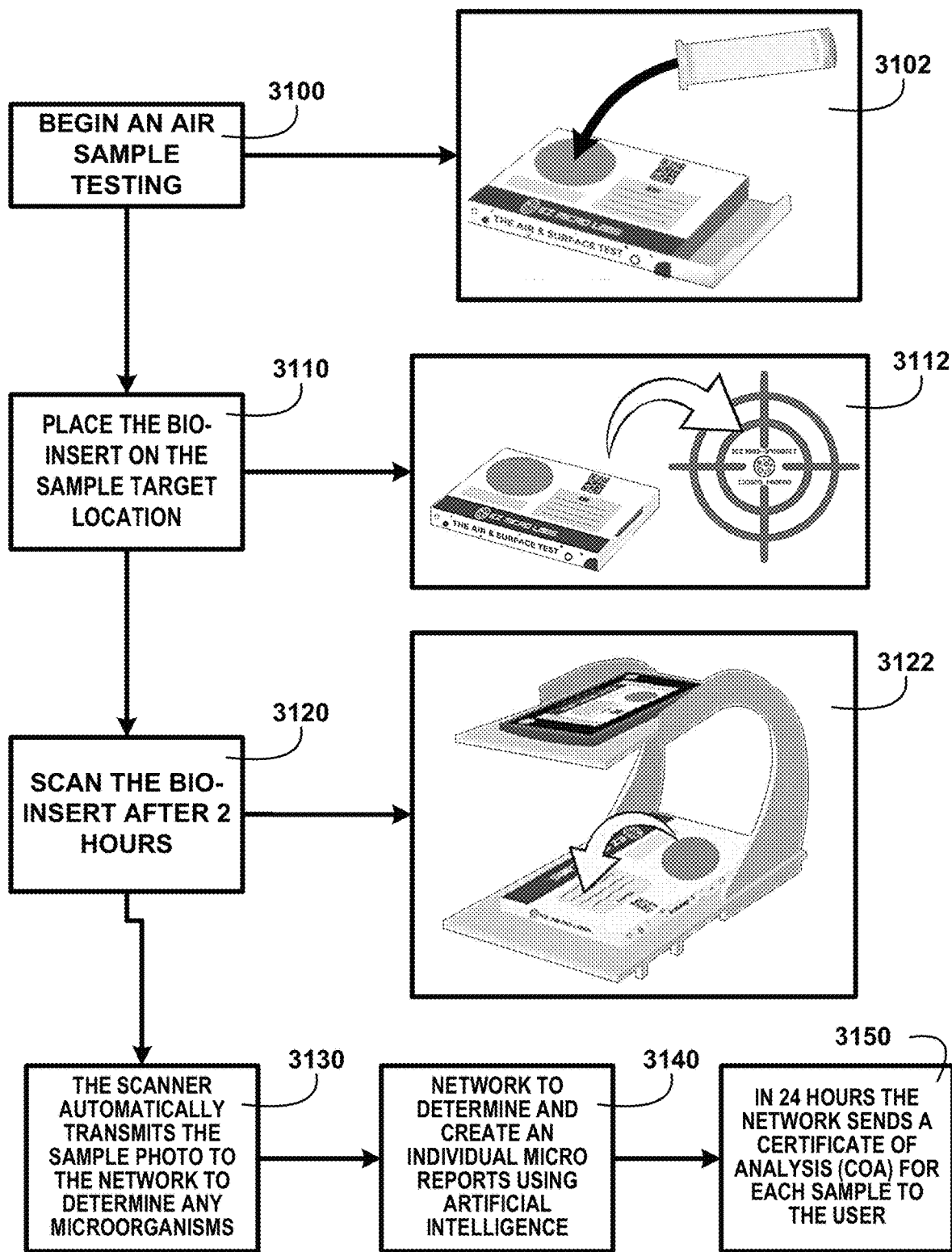
FIG. 31 shows for illustrative purposes only an example of an air test process of one embodiment.

An Air Test Process:

FIG. 31 shows for illustrative purpose only an example of an air test process of one embodiment. FIG. 31 shows to begin an air sample testing 3100, the user will put on gloves and the apron, making sure to spray the gloves with 70% isopropyl, rubbing hands together till dry. Take a Bio-Insert out of the rack, remove the lid, and place it on the Bio-Insert for later use. Remove the activating solution from the Bio-Insert, pouring the entire solution evenly onto the plate 3102. Place the empty container back in the box.

The user then places the bio-insert on the sample target location 3110. Let the Bio-insert sit for 2 Hours before collecting 3112. After placing the bio-insert on the target location the user will scan the bio-insert QR code and then scan a permanent location marker closest to the test target location to link a location. The user will scan the bio-insert after 2 hours 3120. The user will place the scanner on the top level of the photo stand scanner support and the bio-insert being tested on the bottom level 3122 to standardize the focal length and image size for analysis.

The user presses the capture button to capture a photo of the bio-insert plated test area. The scanner automatically transmits the sample photo to the network to determine any microorganisms 3130. The transmitted photo is received by the network to determine and create an individual micro report using artificial intelligence 3140. In 24 hours, the network sends a certificate of analysis (COA) for each sample to the user 3150 of one embodiment.

Figure 32:
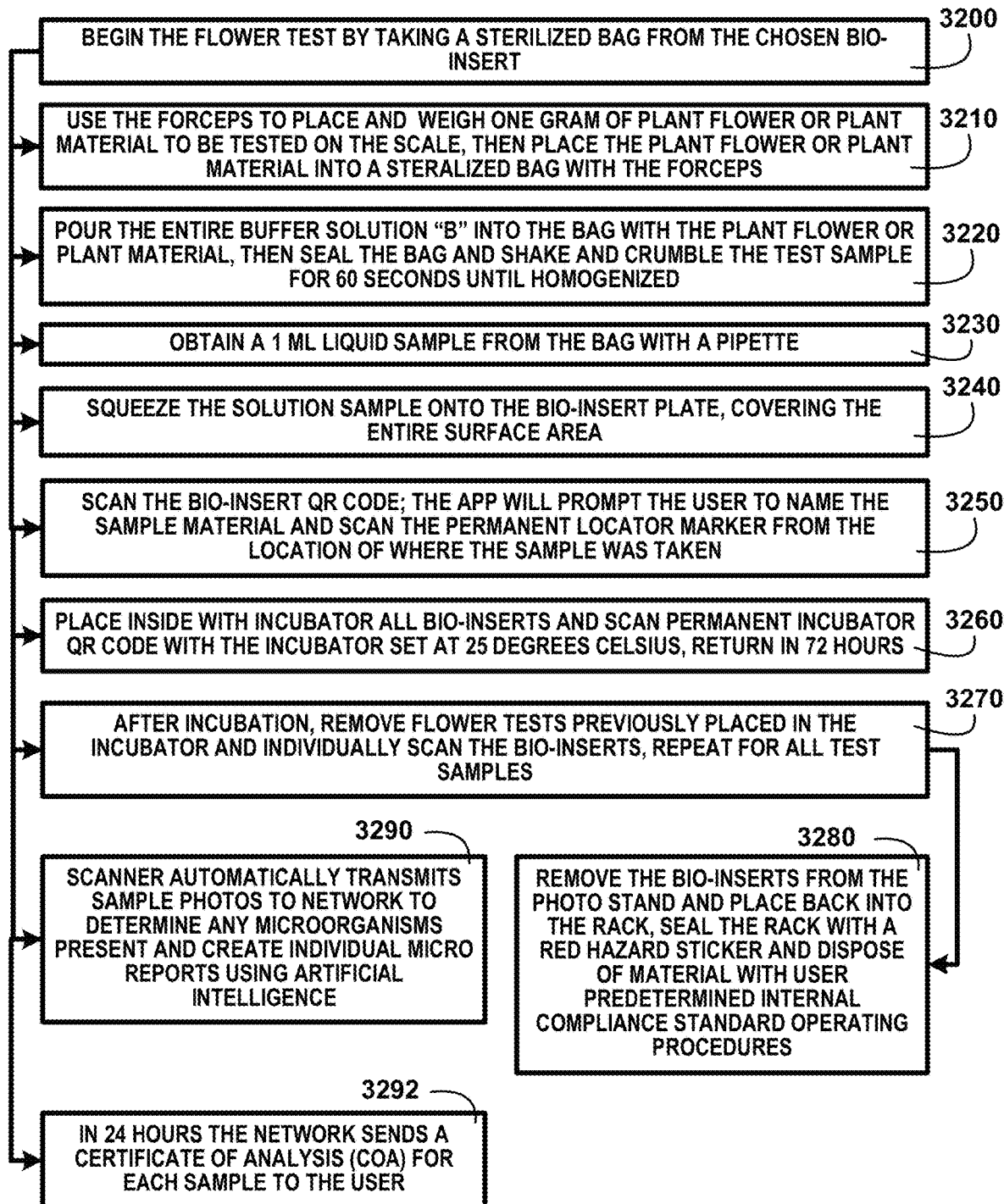
FIG. 32 shows a block diagram of an overview of a flower test process of one embodiment.

A Flower Test Process:

FIG. 32 shows a block diagram of an overview of a flower test process of one embodiment. FIG. 32 shows the flower test process that will begin the flower test by taking a sterilized bag from the chosen bio-insert 3200. The user will use the forceps to place and weigh one gram of plant flower or plant material to be tested on the scale, then place the plant flower or plant material into a sterilized bag with the forceps 3210. The process continues with a user pouring the entire buffer solution "B" into the bag with the plant flower or plant material, then sealing the bag and shaking and crumbling the test sample for 60 seconds until homogenized 3220.

The user will obtain a 1 ml liquid sample from the bag with a pipette 3230, then proceed to squeeze the solution sample onto the bio-insert plate, covering the entire surface area 3240. The user will scan the bio-insert QR code; the app will prompt the user to name the sample material and scan the permanent locator marker from the location where the sample was taken 3250. The next step is to place all inside with incubator all bio-inserts and scan the permanent incubator QR code with the incubator set at 25 degrees Celsius, and return in 72 hours 3260.

After incubation, the user proceeds to remove flower tests previously placed in the incubator individually scan the bio-inserts, and repeat for all test samples 3270. After scanning each test sample, the user will remove the bio-inserts from the photo stand and place them back into the rack, seal the rack with a red hazard sticker, and dispose of material with user predetermined internal compliance standard operating procedures 3280. The scanner automatically transmits sample photos to the network to determine any microorganisms present and create individual micro reports using artificial intelligence 3290. In 24 hours, the network sends a certificate of analysis (COA) for each sample to the user 3292 of one embodiment.

Figure 33:
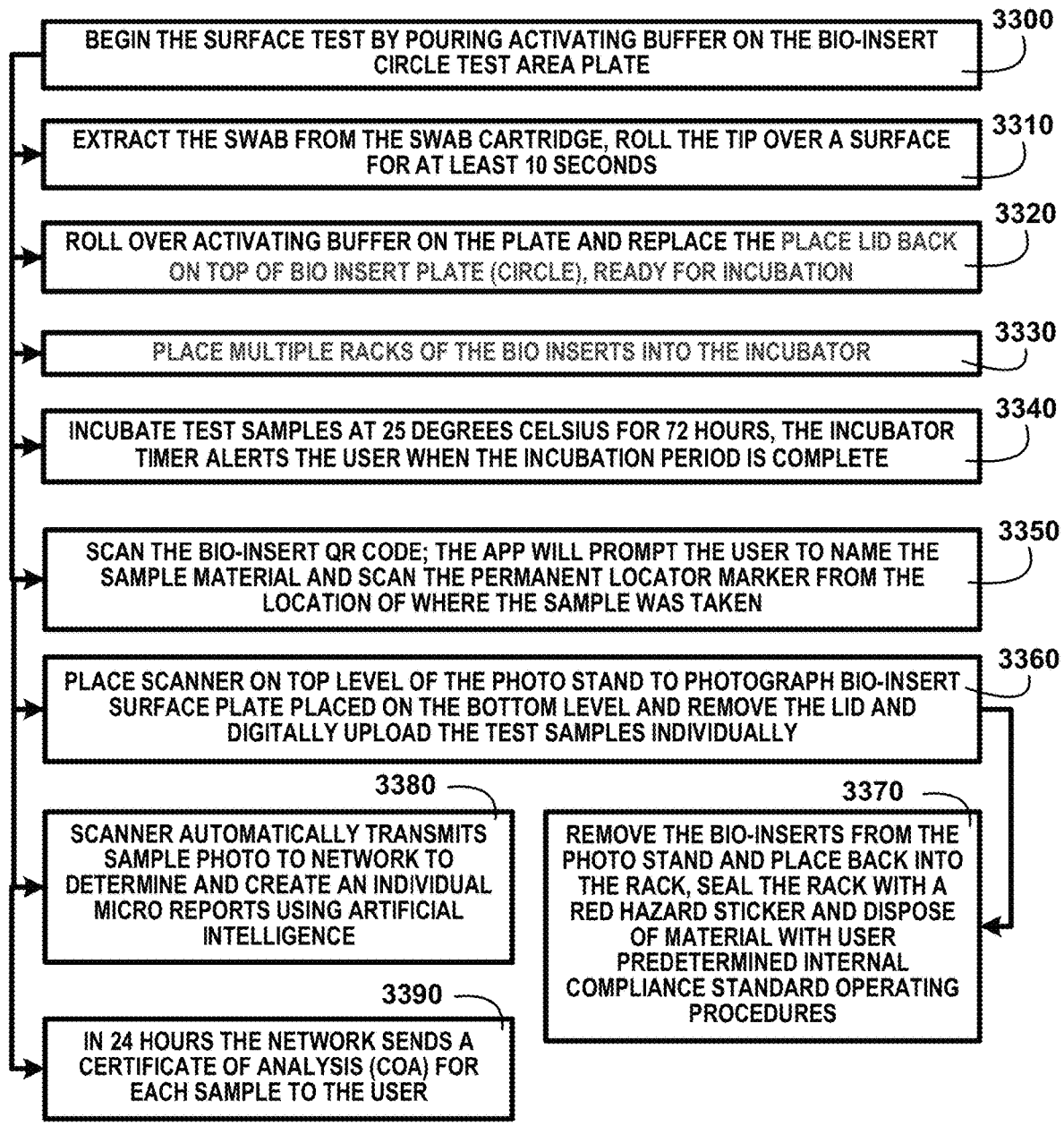
FIG. 33 shows a block diagram of an overview of a swab test process of one embodiment.

A Swab Test Process:

FIG. 33 shows a block diagram of an overview of a swab test process of one embodiment. FIG. 33 shows a swab test process that will begin the surface test by pouring activating buffer on the bio-insert circle test area plate 3300. The user will extract the swab from the swab cartridge, and roll the tip over the surface for at least 10 seconds 3310. The user will roll over the activating buffer on the plate and replace the place lid on top of the bio insert plate (circle), ready for incubation 3320. Collect the surface test samples and place multiple racks of the bio inserts into the incubator 3330.

The user will incubate test samples at 25 degrees Celsius for 72 hours, the incubator timer alerts the user when the incubation period is complete 3340. The user proceeds to scan the bio-insert QR code; the app will prompt the user to name the sample material and scan the permanent locator marker from the location where the sample was taken 3350. After the scanning, the user will place the scanner on the top level of the photo stand to photograph the bio-insert surface plate placed on the bottom level and remove the lid, and digitally upload the test samples individually 3360.

After photographing each test sample, the user will remove the bio-inserts from the photo stand and place them back into the rack, seal the rack with a red hazard sticker, and dispose of material with user predetermined internal compliance standard operating procedures 3370. The scanner automatically transmits sample photos to the network to determine and create individual micro reports using artificial intelligence 3380. In 24 hours, the network sends a certificate of analysis (COA) for each sample to the user 3390 of one embodiment.

Website Application:

In one embodiment, a website application is provided in addition to mobile application for computer access to the learning center, reporting of testing information and photograph, receiving coa reports, and ordering kits and supplies. The user gains access using the same account information and logins that are used for the mobile application.

AI and Machine Learning:

In one embodiment, artificial intelligence (AI) algorithms to determine image processing detection of colony counts by automated machine learning models, self-learning and evolving over more data accumulation. The artificial intelligence device machine learning application is taught using analysis with mathematical models of data to identify patterns of known harmful microorganisms stored on at least one database coupled to the server and uses comparisons of those patterns with organic materials test samples detected mold and bacteria patterns to identify the detected harmful microorganisms. The machine learning accumulation of data is used in the AI algorithms to assist the user in preparing reports on the cultivation and other aspects of the growth and productivity of the cultivation.

X,Y Coordinate Tracking:

In one embodiment, an X, Y coordinate tracking with Cartesian Coordinates (inside facility) and GPS tagging. This will produce many other proactive early detection problem analysis and identification to prevent spreading of any bacterial conditions and infestations. The Cartesian Coordinates with gps tagging will be overlaid on the individual rooms mapped in the facility and identified using the QR code locator markers.

Visualize Heat Maps of concentrated areas with Instantaneous vs Historic Scores. /Any detection of bacterial presence will be visible on a heat map that indicates current detections overlaid on historic detection locations. Repeated incidents of bacterial detections at the same location can assist the user in further investigation of the source(s) of the bacterial appearance to eradicate the persistent source.

Schedule notifications by location over service events, timers to help users find overlooked or required maintenance by location will assist the user in maintaining a regular schedule of maintenance to prevent bacterial growth and infestations.

Assign locations and zones to one or more employee or user for the maintenance and periodic inspections to track the scheduled inspections and testing. Schedule notifications are sent through messaging as reminders of the tasks to perform.

The AI system is scheduled to produce trending current testing results vs historic comparisons periodically to gage progress in controlling bacterial detection. Dashboard level NetworkOperation Kiosk/Screens are placed at critical locations. The dashboard kiosks will monitor multiple facilities. The displayed information will include high level aggregate summaries, drill down to hierarchy level related sub-location/zones. The visualizations at critical locations being easily seen by employees and users will keep them abreast of progress being made and remind them of the vigilance in testing and disinfection of all surfaces and equipment to maintain a bacterial free environment leading to increased productivity.

Gamification Dashboards, Scoreboards to introduce goal and competitive improvement results/score tracking. Tracking and displaying adherence to completing tasks in a timely manner for each employee and use is a method to motivate and engage users. Different shifts can compete with other shifts to achieve a higher score. Different sets of tasked can be grouped where individuals can compete to score higher scores that their counterparts performing the same or similar group of tasks.

Sensors to Detect Bacteria:

In one embodiment, the facility is fitted with various types of sensors to detect bacterial presence. The type of sensor may be different at different locations within the facility. The different types of sensors includes autofluorescence Imaging, fluorescence sensor integrate into goggles, Light-emitting diodes (LEDs) causing illuminated samples to fluoresce without destroying them, Paper-based sensors for bacteria detection, culture-based assays, polymerase chain reaction detection, UV Flashlight Black Light detectors, detecting bacteria using fluorescence-based dyes, optical, mechanical, or electrical biosensors, surface plasmon resonance (SPR) biosensors, mechanical biosensors based on quartz crystal microbalance (QCM) or cantilever technology without the need for sample processing or extra reagents, Electrochemical biosensors comprising potentiometric, amperometric, and impedimetric sensing techniques, and many others using lasers and other optical detection techniques.

Bacterial Treatments:

Bacterial treatments of numerous embodiments are used to eradicate bacterial infestations. The treatments include applying preventive sprays of copper-based bactericides to infestations will kill bacteria. The kit includes isopropyl alcohol in a spray bottle to disinfect surfaces and equipment. Organic fungicides and bactericides that do not damage healthy plant materials is used to control bacteria infestations without damaging the health balance of the plant. Ozonated water in the form of droplets and mist is applied to the entire plant to eradicate bacteria without damage the healthy section of the plant.

Scanner Application:

The scanner application, in one embodiment, includes bacterial detection software and sensor detection. Optical detection technologies integrated into the scanner device can detect bacteria and the corresponding analyzer and signal transmission system display the type of bacteria and other data detected. The scanner device camera is used to photograph the detected bacteria.

The foregoing has described the principles, embodiments, and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

What is claimed is:

1. A portable microbial test kit for testing organic plant materials, comprising:
   a plurality of QR code identifiers, each being removably coupled to a surface adjacent to a testing location and at least one plant material in a facility;
   an air and surface test kit at the testing location configured to combine a collected sample of unknown material from the surface with a microorganism growth stimulator solution to form a first prepared sample;
   a flower test kit at the testing location configured combine a portion of the at least one plant material with a yeast/mold rapid (YMR) activating mold growth solution to accelerate mold growth for mold detection to form a second prepared sample;
   a mobile application operating on a mobile device and coupled to a remote server and an image capture scanner and configured to capture images of the first and second prepared samples and to transmit the captured images to the remote server, wherein the image capture scanner is further configured to scan at least one of the plurality of QR code identifiers to determine a location of the first and second prepared samples;

a plurality of sensors coupled to the mobile application and located at different locations within the testing facility and configured to detect environmental conditions in the testing facility at the different locations and assigned to at least one of the plurality of QR code identifiers;

wherein the remote server is coupled to a database and a processor and configured to receive the captured images for analyzing and comparing the captured images to known harmful microorganisms to create results identifying matching patterns that indicate a presence of the known harmful microorganisms at the testing location;

a graphical user interface coupled to the mobile application and configured to display an alert to a user of an infestation of the known harmful microorganisms, to display the results to the user with at least one treatment recommendation based on the known harmful microorganisms at the testing location and the detected environmental conditions for allowing the user to mitigate infestation of the known harmful microorganisms at the testing location and to prevent spreading of the infestation within the testing facility; and wherein the graphical user interface is further configured to display a map of the facility of the at least one of the plurality of QR code identifiers associated with the identified known harmful microorganisms at the testing location within the facility.

2. The portable microbial test kit for testing organic plant materials of claim 1, wherein the mobile application monitors the plurality of sensors at predetermined intervals to mitigate harmful microorganism infestations.

3. The portable microbial test kit for testing organic plant materials of claim 1, further comprising an incubator wirelessly coupled to the mobile application configured to heat the first and second prepared samples to accelerate microorganism growth.

4. The portable microbial test kit for testing organic plant materials of claim 1, wherein the mobile application generates a retest alert to the user when the comparison identifies what species of microorganism is detected.

5. The portable microbial test kit for testing organic plant materials of claim 1, further comprising a sterilization material to sterilize infected cultivation facility locations to prevent spread of microorganism.

6. The portable microbial test kit for testing organic plant materials of claim 1, further comprising a plurality of sensors wirelessly coupled to the mobile application and positioned at different locations within the cultivation facility configured to detect, identify, track, and measure environmental conditions and the presence of microorganisms at the different locations identified with the at least one of the plurality of QR code identifiers.

7. The portable microbial test kit for testing organic plant materials of claim 1, wherein the known harmful microorganisms includes at least one of *Fusarium, Salmonella*, or *E. coli*.

8. A portable microbial test kit for testing organic plant materials, comprising:

a plurality of QR code identifiers, each being removably coupled to a surface adjacent to a testing location and at least one plant material in a facility;

an air and surface test kit at the testing location configured to combine a collected sample of unknown material from the surface with a microorganism growth stimulator solution to form a first prepared sample;

a flower test kit at the testing location configured combine a portion of the at least one plant material with a yeast/mold rapid (YMR) activating mold growth solution to accelerate mold growth for mold detection to form a second prepared sample;

an incubator located at the testing location and configured to heat the first and second prepared samples to accelerate a microorganism growth;

a mobile application operating on a mobile device and coupled to a remote server and configured to capture images of the first and second prepared samples and to transmit the captured images to the remote server, wherein the image capture scanner is further configured to scan at least one of the plurality of QR code identifiers to determine a location of the first and second prepared samples;

a plurality of sensors coupled to the mobile application and located at different locations within the testing facility and configured to detect environmental conditions in the testing facility at the different locations and assigned to at least one of the plurality of QR code identifiers;

wherein the remote server is coupled to a database and a processor and configured to receive the captured images for analyzing and comparing the captured images to known harmful microorganisms to create results identifying matching patterns that indicate a presence of the known harmful microorganisms at the testing location;

a graphical user interface coupled to the mobile application and configured to display an alert to a user of an infestation of the known harmful microorganisms, to display the results to the user with at least one treatment recommendation based on the known harmful microorganisms at the testing location and the detected environmental conditions for allowing the user to mitigate infestation of the known harmful microorganisms at the testing location and to prevent spreading of the infestation within the testing facility; and wherein the graphical user interface is further configured to display a map of the facility of the at least one of the plurality of QR code identifiers associated with the identified known harmful microorganisms at the testing location within the facility.

9. The portable microbial test kit for testing organic plant materials of claim 8, wherein the plurality of sensors includes at least one of autofluorescence imaging, fluorescence sensing, or light-emitting diodes (LEDs), configured to cause illuminated samples to fluoresce without destroying them.

10. The portable microbial test kit for testing organic plant materials of claim 8, wherein the known harmful microorganisms includes at least one of *Fusarium, Salmonella*, or *E. coli*.

11. The portable microbial test kit for testing organic plant materials of claim 8, further comprising a website application operating on a local computer configured to provide access to a learning center, reporting of testing information and photographs, receiving COA reports, and ordering kits and supplies.

12. The portable microbial test kit for testing organic plant materials of claim 8, wherein the mobile application monitors the plurality of sensors at predetermined intervals to mitigate harmful microorganism infestations.

13. The portable microbial test kit for testing organic plant materials of claim 8, wherein the mobile application generates a retest alert to the user when the comparison identifies what species of microorganism is detected.

14. The portable microbial test kit for testing organic plant materials of claim 8, wherein the incubator is wirelessly coupled to the mobile application and configured to remotely control the heating of the first and second prepared samples to accelerate microorganism growth.

15. A portable microbial test kit for testing organic plant materials, comprising:
- a plurality of QR code identifiers, each being removably coupled to a surface adjacent to a testing location and at least one plant material in a facility;
- an air and surface test kit at the testing location configured to combine a collected sample of unknown material from the surface with a microorganism growth stimulator solution to form a first prepared sample;
- a flower test kit at the testing location configured combine a portion of the at least one plant material with a yeast/mold rapid (YMR) activating mold growth solution to accelerate mold growth for mold detection to form a second prepared sample;
- an incubator located at the testing location configured to heat the first and second prepared samples to accelerate a microorganism growth;
- a mobile application operating on a mobile device and coupled to a remote server and an image capture scanner and configured to capture images of the first and second prepared samples and to transmit the captured images to the remote server, wherein the image capture scanner is further configured to scan at least one of the plurality of QR code identifiers to determine a location of the first and second prepared samples;
- a plurality of sensors coupled to the mobile application and located at different locations within the testing facility and configured to detect environmental conditions in the testing facility at the different locations and assigned to at least one of the plurality of QR code identifiers;
- wherein the remote server is coupled to a database and a processor and configured to receive the captured images for analyzing and comparing the captured images to known harmful microorganisms to create results identifying matching patterns that indicate a presence of the known harmful microorganisms at the testing location;
- a graphical user interface coupled to the mobile application and configured to display an alert to a user of an infestation of the known harmful microorganisms, to display the results to the user with at least one treatment recommendation based on the known harmful microorganisms at the testing location and the detected environmental conditions for allowing the user to mitigate infestation of the known harmful microorganisms at the testing location and to prevent spreading of the infestation within the testing facility and to generate a retest alert to the user when the comparison identifies what species of microorganism is detected; and
- wherein the graphical user interface is further configured to display a map of the facility of the at least one of the plurality of QR code identifiers associated with the identified known harmful microorganisms at the testing location within the facility.

16. The portable microbial test kit for testing organic plant materials of claim 15, wherein the known harmful microorganisms includes at least one of *Fusarium, Aspergillus, Salmonella, E. coli, Lister, S Arueu, Mucor*, or *P. aeruginosa*.

17. The portable microbial test kit for testing organic plant materials of claim 15, wherein the mobile application monitors the plurality of sensors at predetermined intervals to mitigate harmful microorganism infestations.

18. The portable microbial test kit for testing organic plant materials of claim 15, wherein the plurality of sensors includes at least one of autofluorescence imaging, fluorescence sensing, or light-emitting diodes (LEDs), configured to cause illuminated samples to fluoresce without destroying them.

19. The portable microbial test kit for testing organic plant materials of claim 15, wherein the plurality of sensors includes at least one of an optical, mechanical, or electrical biosensor or a surface plasmon resonance (SPR) biosensor.

20. The portable microbial test kit for testing organic plant materials of claim 15, wherein the plurality of sensors includes a plurality of UV flashlight black light detectors.

* * * * *